(12) United States Patent
Seki et al.

(10) Patent No.: US 7,993,581 B2
(45) Date of Patent: Aug. 9, 2011

(54) IMMUNOASSAY SYSTEM AND IMMUNOASSAY METHOD

(75) Inventors: Yusuke Seki, Tokyo (JP); Akira Tsukamoto, Toda (JP); Daisuke Suzuki, Tokyo (JP); Masahiro Yamaoka, Tokyo (JP); Nami Sugita, Ranzan (JP); Akihiko Kandori, Tokyo (JP); Kazuo Saitoh, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1438 days.

(21) Appl. No.: 11/006,757

(22) Filed: Dec. 8, 2004

(65) Prior Publication Data

US 2005/0202572 A1    Sep. 15, 2005

(30) Foreign Application Priority Data

Mar. 11, 2004    (JP) ................................ 2004-068645

(51) Int. Cl.
*G01N 1/36* (2006.01)
*G01N 33/553* (2006.01)

(52) U.S. Cl. .............. 422/50; 436/526; 422/64; 422/65; 422/186.01

(58) Field of Classification Search ..................... 422/50, 422/64, 65, 186.01; 436/526
See application file for complete search history.

(56) References Cited

U.S. PATENT DOCUMENTS

| | | | | |
|---|---|---|---|---|
| 5,149,967 A | * | 9/1992 | Otaka | 250/310 |
| 5,473,249 A | * | 12/1995 | Chaussy et al. | 324/248 |
| 5,985,672 A | * | 11/1999 | Kegelman et al. | 436/50 |
| 6,084,399 A | * | 7/2000 | Nagaishi et al. | 324/204 |
| 6,123,902 A | * | 9/2000 | Koch et al. | 422/50 |
| 6,483,303 B2 | * | 11/2002 | Simmonds et al. | 324/239 |

FOREIGN PATENT DOCUMENTS

| | | |
|---|---|---|
| JP | 59-96785 | 11/1982 |
| JP | 5-264556 | 3/1992 |

(Continued)

OTHER PUBLICATIONS

Keiji Enpuku, "Biological Immunoassay with Magnetic Marker and SQUID Magnetometer", oyo Buturi, vol. 73, No. 1, 2004, pp. 28-31, with English abstract.

(Continued)

*Primary Examiner* — Jacob Cheu
*Assistant Examiner* — Pensee Do
(74) *Attorney, Agent, or Firm* — Stites & Harbison PLLC; Juan Carlos A. Marquez, Esq.

(57) ABSTRACT

The present invention provides an immunoassay technique which enables efficient detection of antigen-antibody reaction with high sensitivity by a magnetic method using magnetic particles and a SQUID magnetic sensor or sensors. A system based on the technique includes a disk-shaped sample holder which holds on a circle a plurality of sample containers for accommodating marked samples, resulting from marking of samples with magnetic particles by antigen-antibody reaction; rotating means for rotating the holder around its central shaft; magnetizing means for magnetizing the marked samples outside a magnetic shield; and a magnetic sensor for detecting, within the magnetic shield, magnetic fields generated from the marked samples which have been magnetized. By rotation of the holder, areas fixing and holding different ones of the sample containers are successively inserted into the magnetic shield, and the magnetization of the marked samples accommodated in first ones of the sample containers and the detection of magnetic fields generated from the marked samples accommodated in second ones of the sample containers are executed in parallel.

14 Claims, 21 Drawing Sheets

FOREIGN PATENT DOCUMENTS

| | | |
|---|---|---|
| JP | 10-513551 | 1/1996 |
| JP | 11-508031 | 2/1996 |
| JP | 2001-524675 | 8/1998 |
| JP | 2001-033455 | 7/1999 |
| JP | 2001-133458 | 11/1999 |
| JP | 2003-515743 | 11/2000 |
| JP | 2003-035758 | 7/2001 |
| JP | 2003-207511 | 1/2002 |
| WO | WO 96/23227 | 1/1996 |
| WO | WO 96/27133 | 2/1996 |
| WO | WO 97/40377 | 3/1997 |
| WO | WO 99/27369 | 8/1998 |
| WO | WO 01/40790 | 11/2000 |

OTHER PUBLICATIONS

Keiji Enpuku et al., "Detection of Magnetic Nanoparticles with Superconducting Quantum Interference Device (SQUID) magnetometer and Application to Immunoassays", Jpn. J. Appl. Phys., vol. 38 (1999), pp. 1102-1105.

K. Enpuku et al, "Application of High $T_c$ SQUID Magnetometer to Biological Immunoassays", IEEE Transactions on Applied Superconductivity, vol. 11, No. 1, Mar. 2001, pp. 661-664.

Y. R. Chemla et al., :Ultrasensitive Magnetic Biosensor for Homogeneous Immunoassay, PNAS, Dec. 19, 2000, vol. 97, No. 26, pp. 14268-14272.

Andreas Haller, et al., Low $T_c$ SQUID Measurement System for magnetic Relaxation Immunoassays in Unshielded Environment:, IEEE Transactions on Applied Superconductivity, vol. 11, No. 1, Mar. 2001, pp. 1371-1374.

SeungKyun Lee et al., "Magnetic Gradiometer Based on a High-Transition Temperature Superconducting Quantum Interference Device for Improved Sensitivity of a Biosensor", Applied Physics Letters, vol. 81, No. 16, Oct. 14, 2002, pp. 3094-3096.

R. Kötitz et al., "SQUID Based Remanence Measurements for Immunoassays", IEEE Transactions on Applied Superconductivity, vol. 7, No. 2, Jun. 1997, pp. 3678-3681.

K. Enpuku et al, "High $T_c$ SQUID System and Magnetic Marker for Biological Immunoassays", IEEE Transactions on Applied Superconductivity, vol. 13, No. 2, Jun. 2003, pp. 371-376.

* cited by examiner

FIG.16

| RESIDUAL MAGNETIZATION MEASUREMENT | ☒ |
|---|---|

FILE NAME
☐ AVERAGE DATA [                    ] REF
☐ MEASUREMENT DATA [                    ] REF

COMMENT
[                    ]

SAMPLE 1 [                    ]
SAMPLE 2 [                    ]
SAMPLE 3 [                    ]
SAMPLE 4 [                    ]
SAMPLE 5 [                    ]
SAMPLE 6 [                    ]
SAMPLE 7 [                    ]
SAMPLE 8 [                    ]
SAMPLE 9 [                    ]
SAMPLE 10 [                    ]
SAMPLE 11 [                    ]
SAMPLE 12 [                    ]

SAMPLING FREQUENCY [2000] Hz   NUMBER OF ADDING [100] TIMES   ROTATIONAL SPEED [60] rpm   WAITING TIME [10] S

[MEASUREMENT START]   [PRINT]   [SHUT DOWN]

[                    ]

IMMUNOASSAY SYSTEM AND IMMUNOASSAY METHOD

CLAIM OF PRIORITY

The present invention claims priority from Japanese application JP 2004-068645 filed on Mar. 11, 2004, the content of which is hereby incorporated by reference into this application.

BACKGROUND OF THE INVENTION

The present invention relates to an immunoassay technique of magnetically detecting antigen-antibody reactions by using magnetic particles and a superconducting quantum interference device (SQUID) magnetic sensor.

Today, requirements are increasing for high-sensitivity detection of such objects as various pathogenic bacteria, cancer cells, DNAs and environmentally harmful substances by immune reactions, and many attempts have been made to develop immunoassay systems to meet these requirements. Common immunoassay methods include an optical technique by which a detective antibody which selectively combines with the antigen to be detected is marked with an optical marker such as a fluorescent enzyme or the like, and optical signals from the optical marker indicating any antigen-antibody combining reaction are detected to identify the type and quantity of the antigen involved. However, optical methods are not adequate in the sensitivity of detection, and require a step to was away uncombined optical markers.

With a view to achieving a higher level of detection sensitivity than optical methods, magnetic methods by which antigen-antibody reactions are detected by using magnetic particles and a SQUID magnetic sensor have come to be proposed in recent years. By such a magnetic method, an antibody for detection use magnetically marked with magnetic particles (hereinafter referred to as magnetic marker) is detected with an extremely sensitive SQUID magnetic sensor.

Methods of detecting magnetic markers will be described below. Methods based on (1) measurement of magnetic susceptibility, (2) measurement of magnetic relaxation or (3) measurement of remanent magnetism are proposed. The following paragraphs will describe (1) through (3).

(1) Method Using Measurement of Magnetic Susceptibility

A DC magnetic field to magnetize magnetic markers is applied in a direction at a right angle to the direction of magnetic flux detection of a SQUID magnetic sensor, and variations in magnetic field generated by the magnetic markers moving within the area of magnetic flux detection of the SQUID magnetic sensor are measured (see, for instance, Japanese Patent Application Laid-Open No. 2001-33455, Keiji Enpuku, the Journal of the (Japanese) Society of Applied Physics, Vol. 73, No. 1, 28 (2004) (in Japanese); K. Enpuku, et al., Jpn. J. Appl. Phys. 38, L1102 (1999); and K. Enpuku, et al., IEEE Trans. Appl. Supercond. 11, 661 (2001)).

Alternatively, an AC magnetic field is applied to a magnetic marker, and the resultant signal is picked up with a SQUID magnetic sensor to detect an antigen-antibody reaction (see, for instance, Japanese Patent Application Laid-Open No. 2001-133458).

(2) Method of Measuring Magnetic Relaxation

The magnetic relaxation from immediately after applying a pulse magnetic field of 1 mT to magnetic markers until one second afterwards is measured. The measurement is carried out in a solution in which uncombined magnetic markers coexist, and combined magnetic markers are detected (see, for instance, Keiji Enpuku, the Journal of the (Japanese) Society of Applied Physics, Vol. 73, No. 1, 28 (2004) (in Japanese); Y. R. Chemla, et al., Proc. National Acad. Sciences of U.S.A. 97, 14268 (2000); A. Haller, et al., IEEE Trans. Appl. Supercond. 11, 1371 (2001); and, S. K. Lee, et al., Appl. Phys. Lett. 81, 3094 (2002)).

A method of quantitatively detecting samples in liquid and solid phases by measuring magnetic relaxation, and chemical compounds for detection by measuring magnetic relaxation, their analysis and their use in immuno-magnetography are also reported (see, for instance, International Application Publication No. 10-513551).

(3) Method of Measuring Remanent Magnetism

When magnetic particles grow in size, the remanent magnetism of the magnetic particles is no longer relaxed. A magnetic field of around 0.1 T is applied to a magnetic marker in a position away from a SQUID magnetic sensor to cause remanent magnetization to occur in the magnetic marker. After that, a substrate mounted with a sample is shifted to have its remanent magnetism measured by the SQUID magnetic sensor (see, for instance, Keiji Enpuku, the Journal of the (Japanese) Society of Applied Physics, Vol. 73, No. 1, 28 (2004); R. Kotitz, et al., IEEE Trans. Appl. Supercond. 7, 3678 (1997); and K. Enpuku, et al., IEEE Trans. Appl. Supercond. 13, 371 (2003)).

A method for quantitative detection of analyzed objects in liquid and solid phases, compounds suitable for this purpose and its use in analytical chemistry is reported (see, for instance, International Application Publication No. 11-508031).

Another report concerns the possibility of high-sensitivity detection of magnetic signals by a SQUID magnetic sensor by cooling magnetic markers, after their magnetization, to restrain the Brownian motion of magnetic particles (see, for instance, Japanese Patent Application Laid-Open No. 2003-207511).

According to still another report, a configuration having a rotating body on which a sample is arranged, a magnet for magnetizing magnetic markers when the sample on the rotating body is rotated and a pickup coil made of a normal conducting member is used for magnetizing the magnetic markers in every rotation and detecting the magnetic field in the position of the pickup coil (see, for instance, Japanese Patent Application Laid-Open No. 2003-35758).

Incidentally, yet other reports concern devices for measuring magnetic particles by using an induction coil as the magnetic sensor instead of a SQUID sensor (see, for instance, International Application Publication Nos. 2001-524675 and 2003-515743).

Specific examples of magnetic method to detect antigen-antibody reactions will be described below (see, for instance, Keiji Enpuku, the Journal of the (Japanese) Society of Applied Physics, Vol. 73, No. 1, 28 (2004).

FIG. 1 schematically illustrate an example of procedure of conventional magnetic immunoassay method using antigen-antibody reactions.

As shown in FIG. 1A, fixed antibodies 101 are fixed to the bottom 102 of a sample container. Then, when a living sample is injected into the sample container, antigens 103 contained in the living sample are selectively combined with the fixed antibodies 101 by antigen-antibody reaction as shown in FIG. 1B. Next, when magnetic markers which mark the antigens 103 are injected into the sample container, they are combined by antigen-antibody reaction with the antigens 103 combined with the fixed antibodies 101 as shown in FIG. 1C. Uncombined magnetic markers 104b which are not combined with the antigens 103 are moved at random by Brownian motion in the solution.

The magnetic markers combined with the antigens 103 by antigen-antibody reaction are denoted by reference numeral 104a. When a magnetic field is applied to the sample in this state in the direction indicated by an arrow in FIG. 1D, the magnetic markers 104a combined with the antigens 103 are magnetized and, even after the applied magnetic field disappears, magnetic signals proportional to the quantity of the antigens 103 are generated by the remanent magnetism of the magnetic markers 104a. By detecting these magnetic signals with the pickup coil 105 of a high-sensitivity SQUID magnetic sensor, the quantity of the antigens to be assessed can be measured.

The uncombined magnetic markers 104b are also magnetized, these magnetic signals from the uncombined magnetic markers 104b are cancelled as these markers are moving at random in the solution, resulting a sum of 0. Thus it is not necessary to wash off the uncombined magnetic markers. Considering that immunoassay using optical markers indispensably needs a washing step, the absence of this washing step is one of the remarkable advantages of immunoassay using magnetic markers.

FIG. 2 schematically illustrates an example of magnetic marker used in a magnetic immunoassay method according to the prior art. The magnetic marker has a structure in which a magnetic particle 201 enveloped in a macromolecule 202 is combined with an antibody 203 for detection use. As the magnetic particle 201, an $Fe_3O_4$ particle of 25 nm in diameter is used. After the macro-monomer is adsorbed by the magnetic particle 201, the structure in which the magnetic particle 201 is enveloped in the macromolecule 202 is realized by subjecting the monomer and the cross-linker to radical copolymerization in a tetrahydrofuran solvent. The diameter of the particle combining the macromolecule 202 and the magnetic particle 201 is about 80 nm.

FIG. 3 illustrates an example of result of immunoassay using remanent magnetism according to the prior art, wherein the relationship between the weight w (pg) of an antigen (IL8: interleukin 8) and a signal magnetic flux $\Phi s$ is shown. The weight of the antigen was varied from 0.1 pg to 150 pg, and a good correlation was observed in this range between the two factors. In this experiment, as shown in FIG. 3, the antigen (IL8) was detected down to 0.1 pg. As the molecular weight of IL8 is 10,000, 0.1 pg corresponds to 10 atto mol. Since the quantity of antigen and the signal magnetic flux from the magnetic marker combined with the antigen manifests a certain correlation, the antigen can be detected with high sensitivity by detecting the signal magnetic flux from the magnetic marker with a SQUID, which is a high-sensitivity magnetic sensor.

SUMMARY OF THE INVENTION

In order to make an immunoassay system by a magnetic method using a magnetic marker useful for practical purposes, it is required to measure many samples efficiently. Even though magnetic methods are superior to optical methods in sensitivity, they cannot be considered practically useful in blood tests and the like, in which a large number of samples are measured, as long as they are inferior in the efficiency of testing. In conventional magnetic methods, the emphasis is placed on how magnetic marker in very small quantities can be measured, but no specific proposal has been made on any magnetic method intended for measurement of a large number of samples.

By conventional magnetic methods, measurement is done with the living sample or the container to accommodate the magnetic marker either fixed or linearly moved. The mechanism for linear movement inevitably requires reversal of the moving direction, and the moving speed varies at the time the moving direction is reversed, making the mechanism unsuitable for measurement of many living samples in a short period of time.

Although the device described in the above-cited patent reference (the Japanese Published Unexamined Patent Application No. 2001-33455) is provided with carrying means for moving samples within the area of magnetic flux detection of a SQUID magnetic sensor, this is not intended for measuring a large number of samples. Furthermore, as the magnetizing coil is disposed within a magnetic shield, adjustment is needed to form immediately underneath the SQUID magnetic sensor a magnetic field which is substantially uniform in the horizontal direction by canceling the vertical component of the magnetic field generated by the magnetizing coil with a compensating coil which generates a magnetic field to cancel the magnetic field in the direction parallel to the magnetic flux detected by the SQUID magnetic sensor.

According to the technique described in the above-cited patent reference (see Embodiment 10 in the Japanese Published Unexamined Patent Application No. 2003-35758), the sample is rotated around a rotation axis, a magnetic field is detected at every rotation in the position of a normal conducting pickup coil, and the detected values are added and averaged. It is preferable for the rotation speed to be matched to the band wherein the measurement is desired to be conducted, for instance, 10 kHz. Although the frequency of rotation is preferably not less than 10000 rotations a second (600000 rpm) where the band is 10 kHz, in practice this speed of rotation is difficult to achieve, the S/N ratio should be improved by increasing the number of additions. Incidentally, the above-cited patent reference (the Japanese Published Unexamined Patent Application No. 2003-35758) makes no mention measuring a large number of samples.

Systems of immunoassay by any magnetic method involves a common problem that, where a carrying means is used, a magnetic field generated by the carrying means (for instance by its driving motor or the like) becomes magnetic noise.

In order to make a system of immunoassay by a magnetic method available for practical use, it is conceivable to mount a large number of sample containers for accommodating samples on a sample container mounting base and successively conduct measurements regarding the sample in each sample container. However, if the distance between adjacent sample containers is too short, magnetic signals generated by magnetic markers may interfere with each other. Or if the distance between the sample containers is too long, the efficiency of measurement will be adversely affected. Furthermore, if matching with the performance of the control device for the measuring procedure and that of the data processor for the measured signals are taken into account, it will be difficult to realize a satisfactory system at low cost.

An object of the present invention, attempted in view of these problems, is to provide an immunoassay technique capable of efficiently detect antigen-antibody reactions with high sensitivity by a magnetic method using magnetic particles and a SQUID magnetic sensor.

In order to achieve the object stated above, the invention uses the following configuration.

Thus, a magnet or a magnetic filed generating coil is arranged outside a magnetic shield as a means for applying external magnetic fields to magnetic markers, and a magnetic sensor for detecting the magnetic fields generated from the magnetic markers is arranged within the magnetic shield. A plurality of sample containers for accommodating marked samples, of samples with magnetic particles by antigen-antibody reaction are held on a circle by a disk-shaped sample holder composed of a nonmagnetic substance.

The nonmagnetic disk-shaped sample holder is provided with a mechanism for fixing the plurality of sample containers on a circle. The disk-shaped sample holder can be rotated by a rotating mechanism configured of an ultrasonic motor. A SQUID magnetic sensor is arranged within a magnetic shield device. There are provided a moving mechanism and a positional adjusting mechanism for inserting the disk-shaped sample holder into the magnetic shield device.

In order to detect the rotational position of the disk-shaped sample holder, a mechanism is provided which detects the position by irradiating a marker placed in the peripheral part of the disk-shaped sample holder with a laser beam and reading its reflection with an optical sensor. So that part of the disk-shaped holder is exposed outside the magnetic shield, holes are bored in part of the magnetic shield to let the disk-shaped holder and the rotating mechanism pass. Even during the measurement of magnetic fields generated from magnetic markers in the sample in a sample container of some position, the configuration allows magnetic markers in the samples in sample containers in other positions to be magnetized by the magnet or the magnetic field generating coil.

The immunoassay system according to the invention has a SQUID which detects magnetic field generated from magnetic markers with high sensitivity, a cryostat for cooling the SQUID, and a drive circuit for driving the SQUID, and also has devices to collect the outputs of the SQUID and display and adds them. It further has a light source for raising the temperature of the SQUID to remove trapped flux by heating the SQUID to or above the transition temperature by irradiating it with a laser beam or light from a halogen lamp. The trapped flux might otherwise give rise to magnetic noise. This removal of trapped flux precedes measurement of magnetic fields.

In the immunoassay system according to the invention, by arranging adjacent sample containers with a distance of at least $d\sqrt{2}$, in other words securing a gap of at least $d\sqrt{2}$, between them where d is the distance between the face of the pickup coil of the SQUID magnetic sensor and the internal bottom of the sample containers, interference between magnetic markers from adjoining sample containers is restrained.

The foregoing description of the immunoassay system according to the invention can be summed up as follows. To facilitate positional control and consecutive measurement of living samples, the system uses a disk-shaped sample holder which can be placed under rotation control by a rotating mechanism. A plurality of sample containers for accommodating living samples are arranged on the same circle, and subjected to positional detection by an optical sensor. Holes are bored in the magnetic shield to let sample containers pass. A mechanism to apply magnetic fields to the samples is arranged outside the magnetic shield to make possible simultaneous measurement and magnetization of samples.

As the rotating mechanism for the disk-shaped sample holder, an ultrasonic motor emitting little magnetic noise is used. For more accurate measurement of magnetic signals from magnetic markers, the disk-shaped sample holder is rotated a plurality of times. Magnetic signals from the magnetic markers are measured at every rotation in a state in which the samples are rotated to make possible addition and averaging. Further, to remove trapped flux, which would invite magnetic noise of the SQUID, in a short period of time, a light source for raising the temperature of the SQUID is provided.

Further by arranging adjacent sample containers at a distance of $d\sqrt{2}$ or more between them, where d is the distance between the face of the pickup coil of the SQUID magnetic sensor and the internal bottom of the sample containers, interference between magnetic signals from magnetic markers in adjoining sample containers is prevented.

In this way, in immunoassay by a magnetic method using magnetic markers, efficient measurement of a large number of living samples is made possible.

According to the invention, there is little magnetic interference between adjoining sample containers, and antigen-antibody reaction among a large number of living samples can be efficiently detected with high sensitivity in a short period of time.

BRIEF DESCRIPTION OF THE DRAWINGS

FIG. 16 shows an example of display screen of setting measurement parameters in the immunoassay system according to the invention;

DETAILED DESCRIPTION OF THE PREFERRED EMBODIMENTS

Preferred embodiments of the present invention will be described in detail below with reference to accompanying drawings.

Figure 1A:
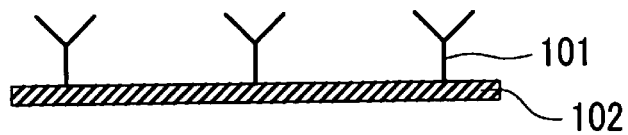
FIG. 1 illustrate an example of procedure of a conventional magnetic immunoassay method using antigen-antibody reaction.
Figure 1B:
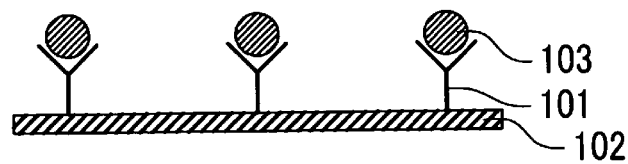
Figure 1C:
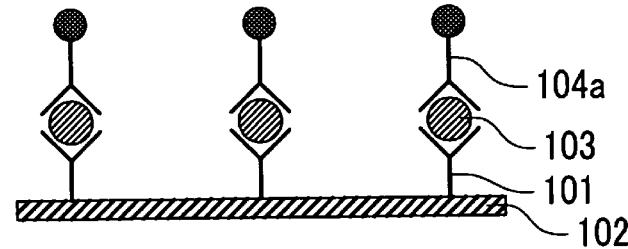
Figure 1D:
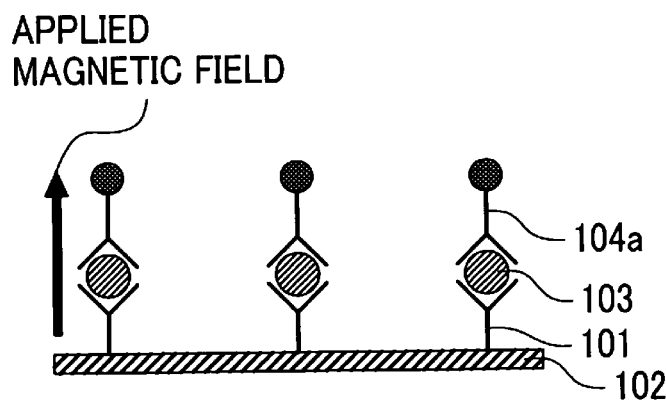
Figure 1E:
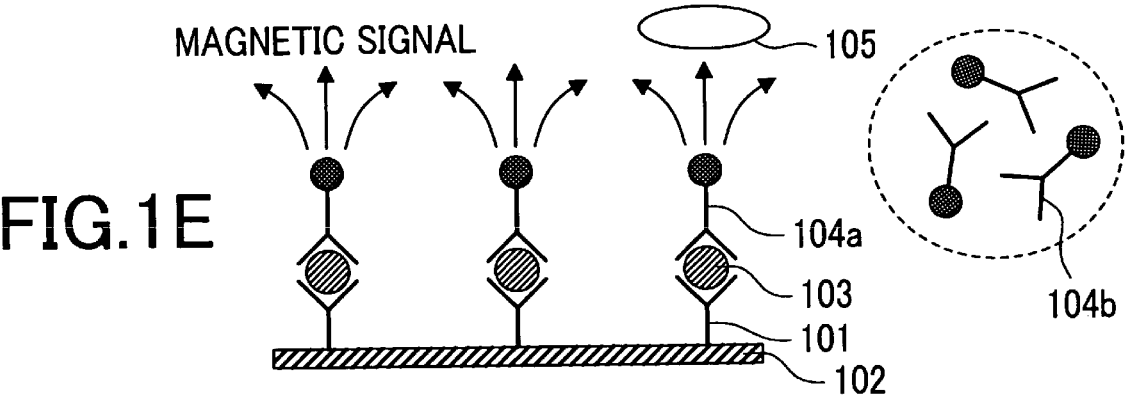
Figure 2:
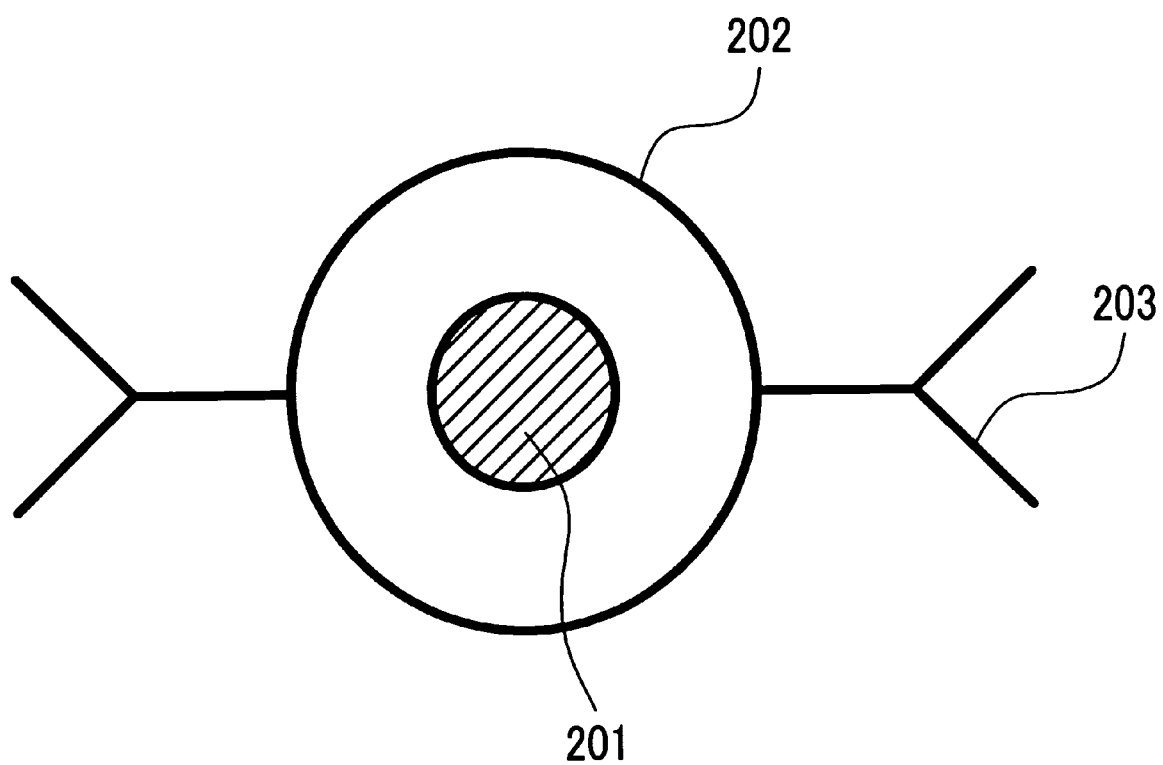
FIG. 2 illustrates an example of magnetic marker used in a magnetic immunoassay method according to the prior art.

The immunoassay system and the immunoassay method to be described as embodying the invention use magnetic markers such as the one shown in FIG. 2, and a procedure magnetic of immunoassay method such as what is shown in FIG. 1 is applied to them. It is desirable from the viewpoint of restraining the infiltration of magnetic noise into measurement that constituent elements for use in the vicinities of magnetic field detection in the immunoassay system embodying the invention be composed of nonmagnetic materials.

Figure 4:
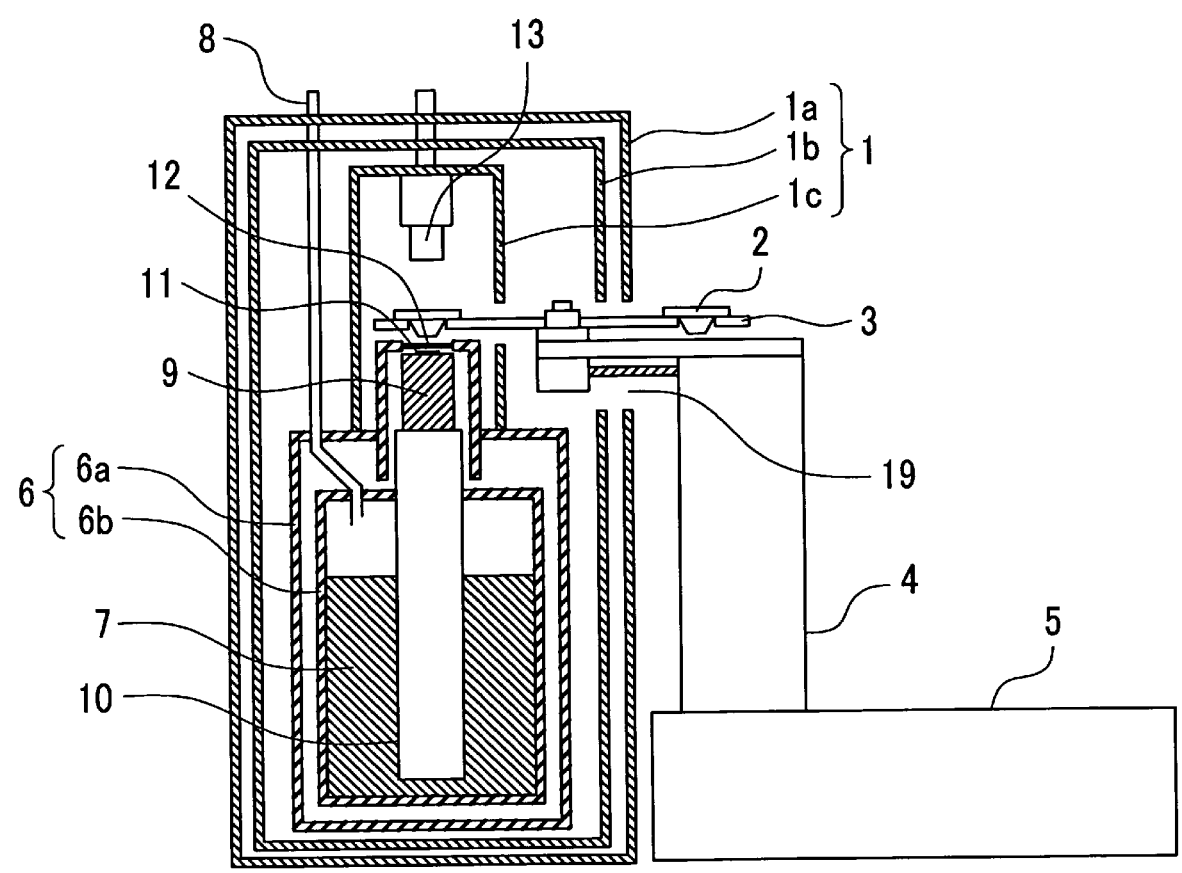
FIG. 4 contains a section of partial configuration of an immunoassay system, which is a preferred embodiment of the present invention, and illustrates the state of arrangement of constituent elements at the time of performing measurement with the system.

FIG. 4 contains a section of partial configuration of the immunoassay system, which is this preferred embodiment of the present invention, and illustrates the state of arrangement of constituent elements at the time of performing measurement with the system.

A plurality of sample containers 2 are fixed on a circle by a nonmagnetic disk-shaped sample holder 3 (hereinafter referred to as simply the sample holder 3). The sample holder 3 is rotated by a rotating mechanism 4. The rotating mechanism 4 is held to be movable in three-dimensional directions over a moving stage 5. The sample holder 3 is moved into magnetic shields 1 by the motion of the rotating mechanism 4 over the moving stage 5 and positionally adjusted.

A high-Te SQUID 11 (hereinafter referred to as simply the SQUID 11) for detecting magnetic signals from magnetic markers is cooled by liquid nitrogen 7 via a sapphire rod 9 and a copper rod 10 to or below a transition temperature, and thermally insulated from the outside by a vacuum insulating container 6 composed of the outer tank 6a of the vacuum insulating container and the inner tank 6b of the vacuum insulating container. The vacuum insulating container 6 is configured of a nonmagnetic material, such as SUS or FRP. Gasified nitrogen is discharged out of and liquefied nitrogen is supplied into the inner tank 6b of the vacuum insulating container 6 via an exhaust and supply port 8. A light source 13 for heating the SQUID is used for heating the SQUID 11 and removing trapped fluxes.

The SQUID 11 is surrounded by the magnetic shields 1 to reduce inputting of ambient magnetic noise. The magnetic shields 1, made of a highly permeable material such as permalloy, have a three-layered structure consisting of magnetic shields 1a, 1b and 1c. It is preferable for the magnetic shields 1 to be structured of multiple layers to enhance their efficiency.

In part of each of the magnetic shields 1 (1a, 1b, 1c) a hole 19 is formed. As shown in FIG. 4, the sample containers 2 and the sample holder 3 are partially exposed to outside the magnetic shields 1 through the holes 19 when measurement is performed.

When replacing any of the sample containers 2 or when adjusting the control circuit of the SQUID 11, the sample holders 3 and the sample containers 2 are fully exposed to outside the magnetic shields 1.

The configuration so far described can reduce the influences of magnetic fields generated by any permanent magnet or any magnetic field applying coil on the SQUID 11.

Thus, it is made possible to apply, while measuring magnetic signals from the magnetic markers in some sample containers 2 within the magnetic shields 1 with the SQUID 11, magnetic fields to the magnetic markers in other sample containers 2 outside the magnetic shields 1. As a result, by rotating the sample holder 3, it is made possible to measure magnetic fields generated by the magnetic marker in sample containers 2 within the magnetic shields 1 and magnetize the magnetic markers in other sample containers 2 outside the magnetic shields 1 at the same time, resulting in a substantial improvement in the efficiency of testing.

Figure 5:
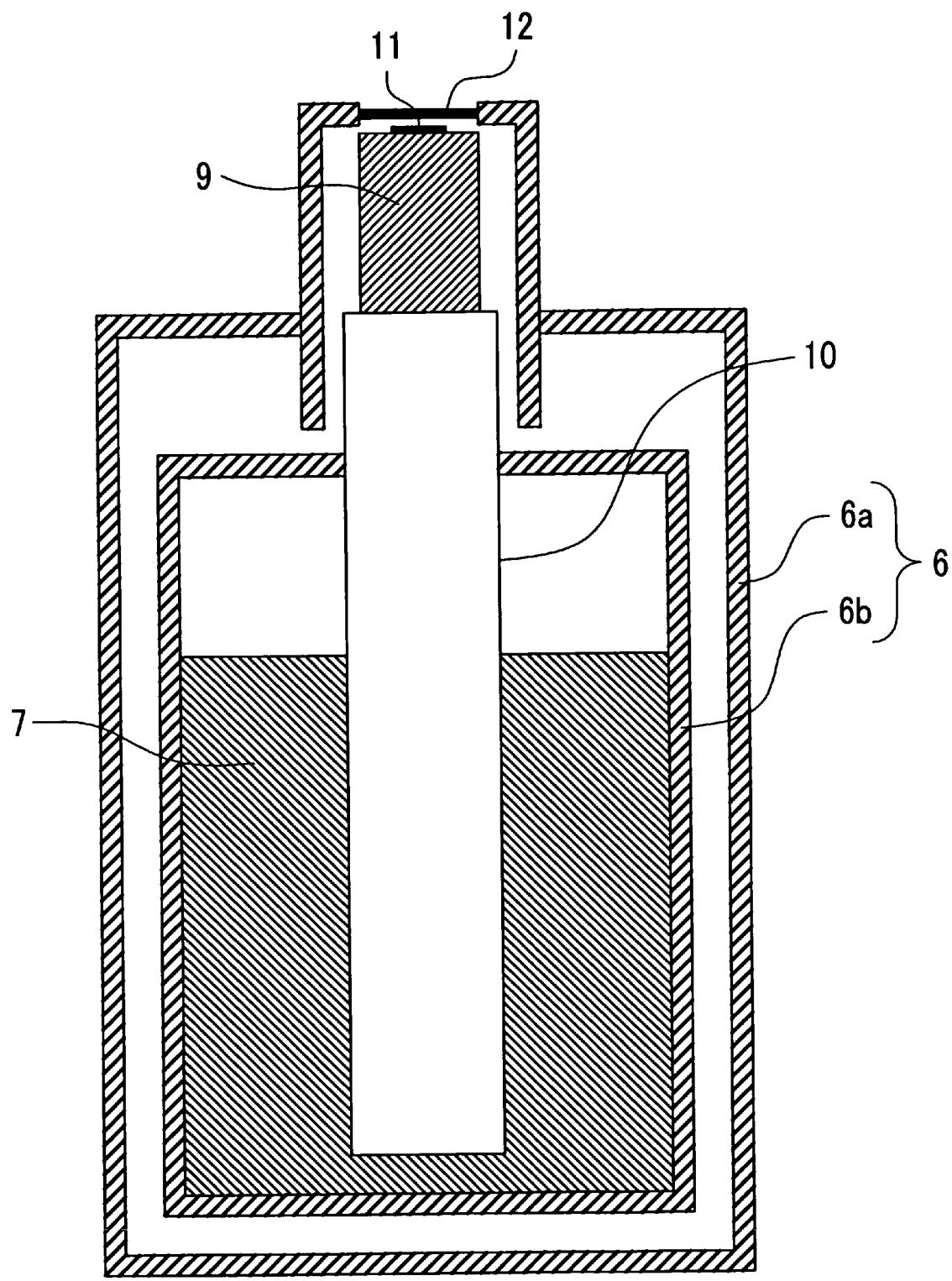
FIG. 5 shows a section of the configuration of a SQUID and a cooling line in the immunoassay system according to the invention.

FIG. 5 shows a section of the configuration of a SQUID and a cooling line in the immunoassay system embodying the invention in this mode, illustrating in particular the SQUID and the cooling line.

In order to shorten the distance between the magnetic marker of each sample container 2 and the SQUID 11 and thereby to enhance the detection sensitivity of magnetic signals and the space resolution, the SQUID 11 is arranged underneath the sample containers 2. As the SQUID 11 is arranged underneath the sample containers 2, the SQUID 11 is not directly cooled by liquefied nitrogen, but is indirectly cooled via the copper rod 10 and the sapphire rod 9, both having high thermal conductivity. The presence of the sapphire rod 9 intervening between the SQUID 11 and the copper rod 10 provides an effect to reduce the influence of magnetic noise generated from the copper rod 10.

The outer tank 6a and the inner tank 6b of the vacuum insulating container 6 are configured of a nonmagnetic material such as SUS or FRP. To shorten the distance between the magnetic marker of each sample container 2 and the SQUID 11, the SQUID 11 and the sample containers 2 are separated from each other by a thin sapphire window 12 of no more than 1 mm in thickness. In order to detect magnetic fields at high efficiency, it is preferable for the distance between the SQUID 11 and the inner bottoms of the sample containers 2 to be not more than 1.5 mm.

Figure 6:
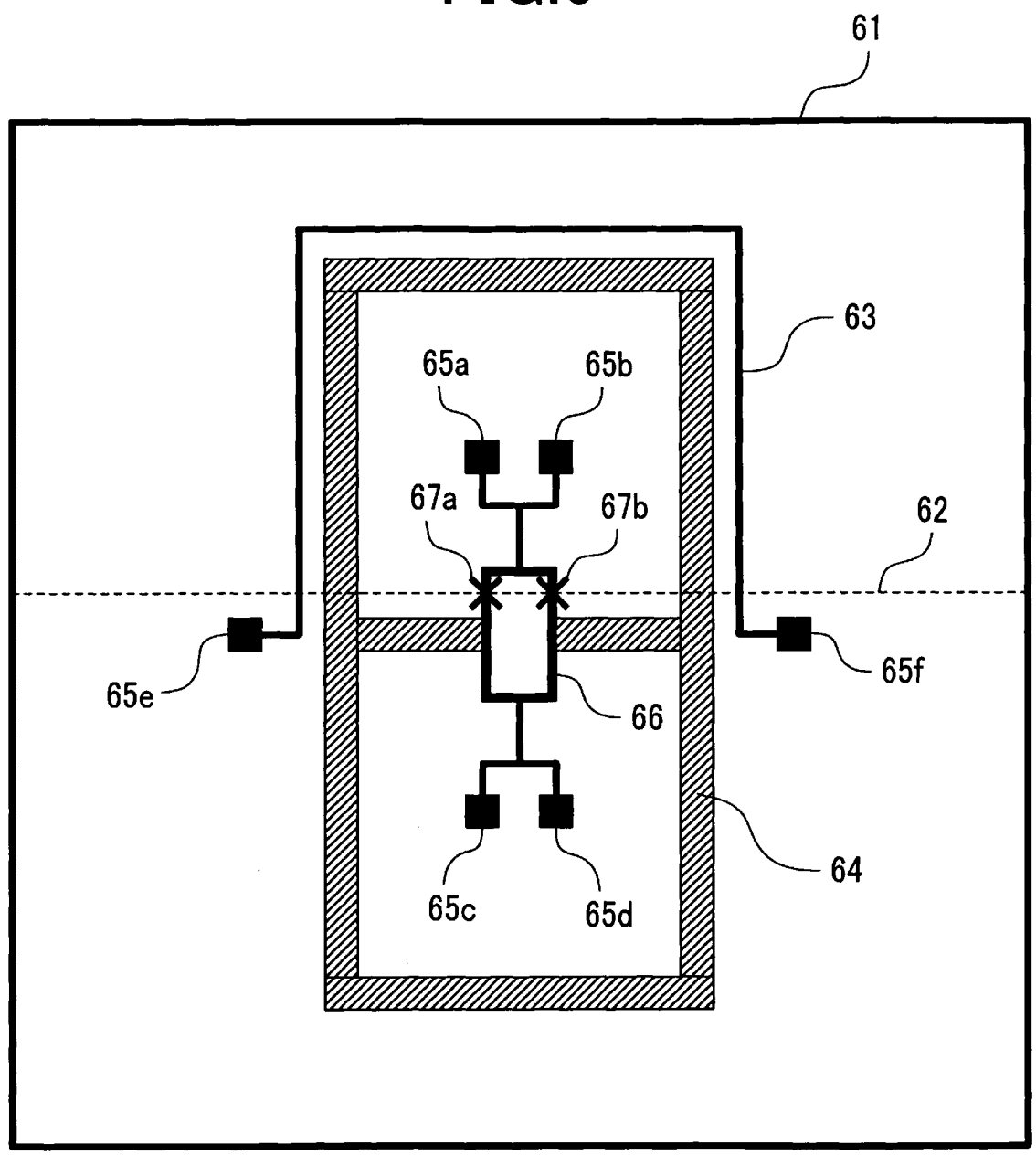
FIG. 6 schematically shows a plan of the configuration of a high-Tc SQUID for use in the immunoassay system according to the invention.

FIG. 6 schematically shows a plan of the configuration of the high-Te SQUID 11 for use in the immunoassay system according to the invention.

A pickup coil 64 and a SQUID ring 66 are configured by forming a film of a high-temperature superconducting material, such as YBa2Cu3Ox, over a substrate 61 made of SrTiO$_3$, MgO or a similar material. The SQUID ring 66 has Josephson junctions 67a and 67b on a bicrystal grain boundary 62 over the substrate 61.

This pickup coil 64 constitutes an 8-shaped differential coil having two loops. When a magnetic flux is inputted to the pickup coil 64, the difference of the induced current arising in each of the loops flows as a current to the SQUID ring 66. This current is inputted to the SQUID ring 66 as a magnetic flux. A feedback coil 63 is formed over the substrate 61, so patterned as to surround one of the loops of the pickup coil 64.

Over the substrate 61, electrodes 65a, 65b, 65c, 65d, 65e and 65f are patterned. As shown in FIG. 6, each of the electrodes 65a, 65b, 65c and 65d is electrically connected to the SQUID ring 66, and each of the electrodes 65e and 65f is electrically connected to the feedback coil 63.

Figure 7:
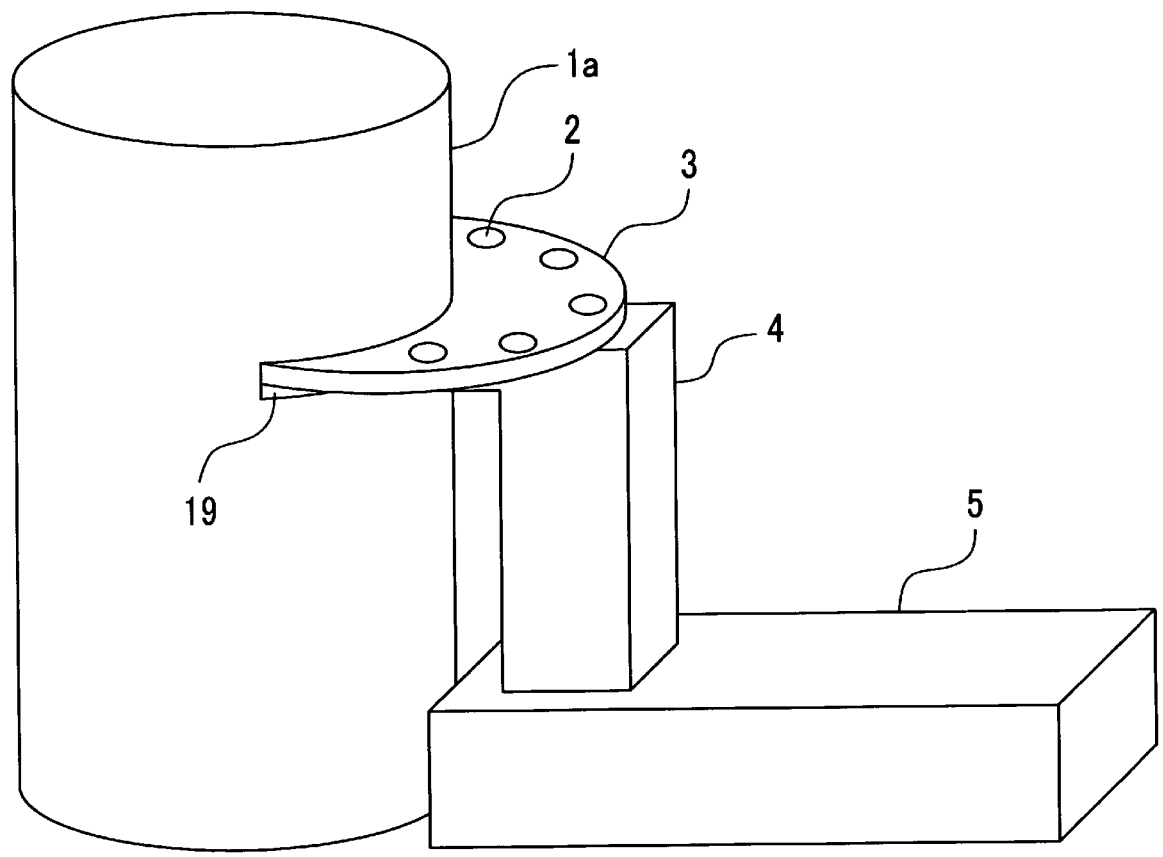
FIG. 7 is a perspective view illustrating the state of arrangement of constituent elements at the time of performing measurement with the immunoassay system according to the invention.

FIG. 7 is a partial perspective view of the immunoassay system embodying the invention in this mode, illustrating the state of arrangement of constituent elements at the time of performing measurement. FIG. 7 matches FIG. 4.

As shown in FIG. 7, when measuring magnetic signals, the sample containers 2 and the sample holder 3 are partially exposed to outside the magnetic shield 1a. This configuration makes it possible to reduce the influence of magnetic fields generated by any permanent magnet or magnetic field applying coil on the SQUID 11.

Thus, it is made possible to apply, while measuring magnetic signals from the magnetic markers in sample containers 2 within the magnetic shields 1 with the SQUID 11, magnetic fields to the magnetic markers in sample containers 2 outside the magnetic shields 1 at the same time or in parallel. As a result, by rotating the sample holder 3, it is made possible to accomplish magnetic field measurement and magnetization at the same time or in parallel, resulting in a substantial improvement in the efficiency of testing.

Figure 8:
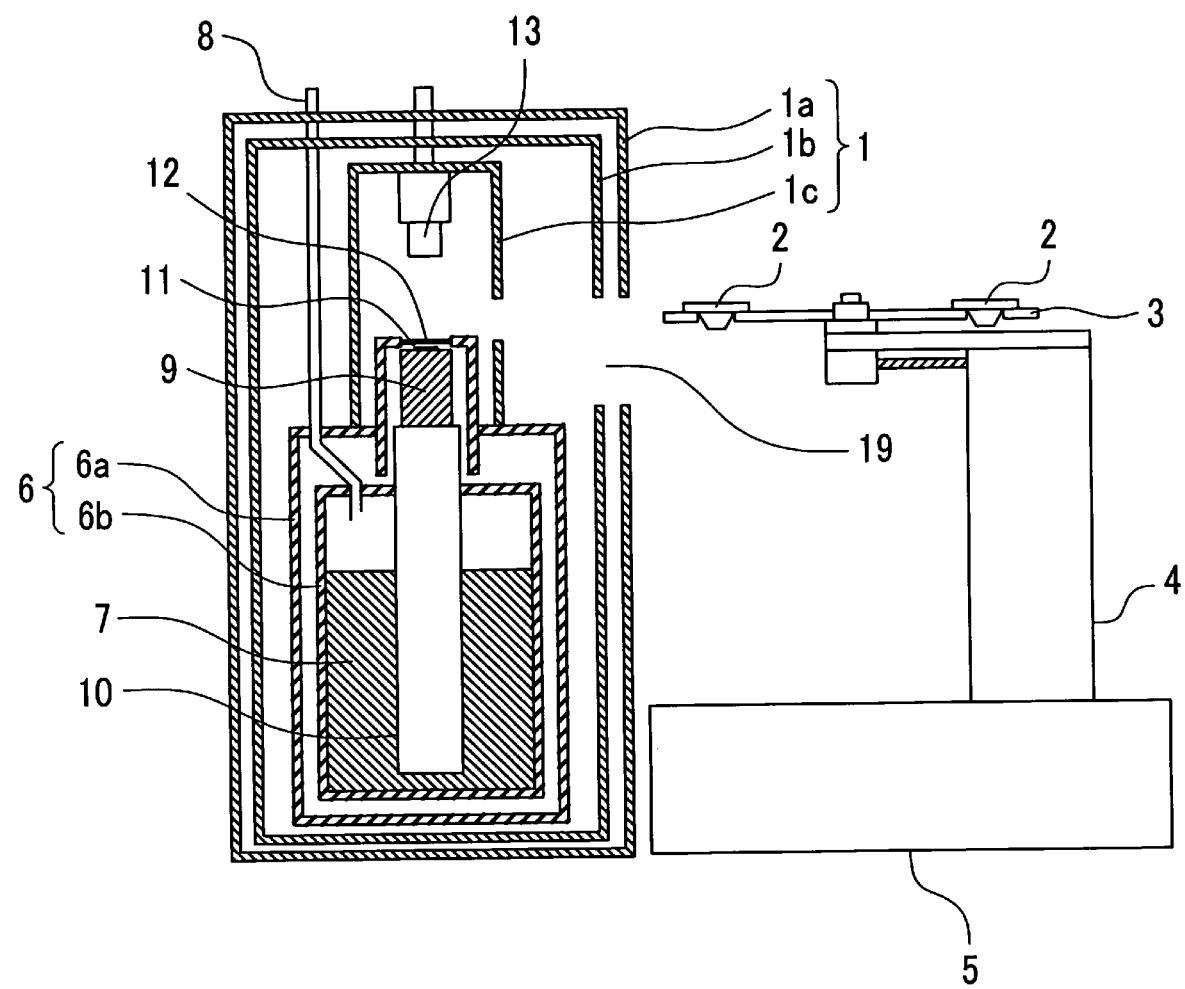
FIG. 8 contains a section of partial configuration of the immunoassay system according to the invention, illustrating the state of arrangement of constituent elements at the time of replacing a sample container and adjusting the control circuit of the high-Tc SQUID.

FIG. 8 contains a section of partial configuration of the immunoassay system embodying the invention in this mode, illustrating the state of arrangement of constituent elements at the time of replacing a sample container 2 and adjusting the control circuit of the high-Tc SQUID 11. FIG. 8 uses common reference numerals with FIG. 4.

The sample containers 2 and the sample holder 3 are moved by the moving stage 5 to outside the magnetic shields 1. The sample containers 2 are replaced in a state in which the sample containers 2 and the sample holder 3 have moved to outside the magnetic shields 1. Also, the control circuit of the SQUID 11 is adjusted in this state. If the self-generated magnetic noise of the SQUID 11 is loud in this state, the SQUID 11 will be heated to or above the transition temperature with the light source 13 for heating the SQUID thereby to remove trapped fluxes. The light source 13 for heating the SQUID is composed of a laser or a halogen lamp. In order to ready the system quickly for performing measurement, it is preferable for the length of time required to heat the SQUID 11 to or above the transition temperature with the light source 13 for heating the SQUID to be not more than a few seconds.

The measuring state shown in FIG. 4 is reached by fixing new sample containers 2 to the sample holder 3 and, after clearing the SQUID 11 of the magnetic flux trap and adjusting the drive circuit for the SQUID, having the moving stage 5 move the sample holder 3 holding the sample containers 2 to inside the magnetic shields 1 through the holes 19 in the magnetic shields 1 (1a, 1b and 1c).

Figure 9:
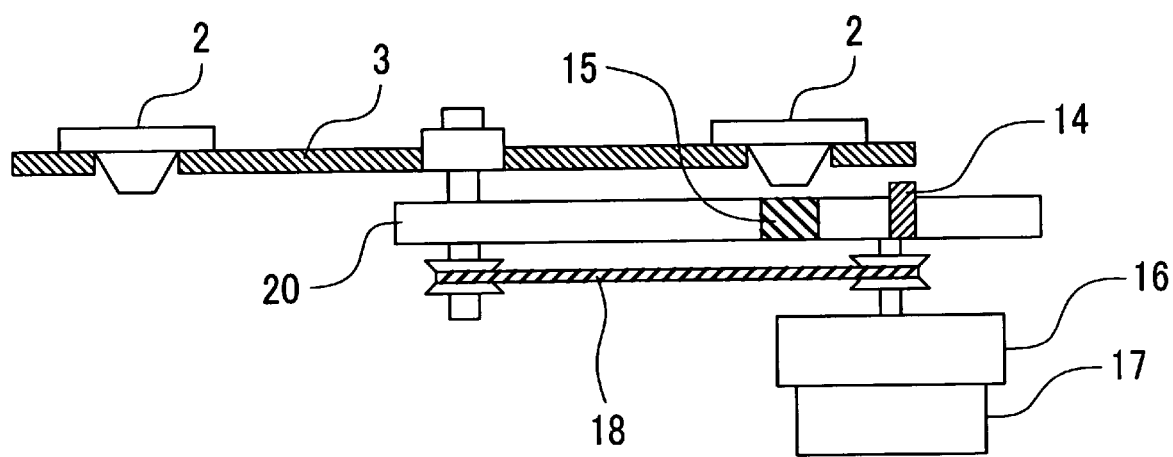
FIG. 9 shows a section of the immunoassay system according to the invention, wherein the configuration of the rotating mechanism for a disk-shaped sample holder and a mechanism for applying magnetic fields is schematically illustrated.

FIG. 9 shows a section of the immunoassay system embodying the invention in this mode, wherein the configuration of the rotating mechanism for the disk-shaped sample holder and the mechanism for applying magnetic fields is schematically illustrated.

The plurality of sample containers 2 are fixed on a circle by the sample holder 3. The sample holder 3 is rotated by an ultrasonic motor 16 via a timing belt 18 held by a support 20. The central shaft of the sample holder 3 is rotatably supported by the support 20. The support 20 is further provided with a position detection sensor 14 and a permanent magnet or an exciting coil 15. An encoder 17 detects the rotation speed of the ultrasonic motor 16. The rotation speed of the ultrasonic motor 16 can be regulated in an approximate range of 10 rotations per minute to 100 rotations per minute.

The position detection sensor 14 detects the position of a marker 42 for position detection (to be described with reference to FIG. 12) formed on either the upper or the lower face of the peripheral part of the sample holder 3 by irradiating the peripheral part of the sample holder 3 with a laser beam and reading its reflection with an optical sensor. The detection of the position of the marker 42 makes possible addition and averaging of magnetic signals, and their addition and averaging makes possible enhancement of the S/N ratio of the magnetic signals. If the rotation speed is 60 rotations a minute, an added and averaged signal can be acquired 60 times a minute.

The magnetic marker in each of the sample containers 2 is magnetized by the magnetic field generated by the permanent magnet or the exciting coil 15. As the method for detecting magnetic markers in the immunoassay system of this embodiment, it is preferable to measure the residual magnetism of magnetic particles in the magnetic markers and/or to measure magnetic relaxation. In order to efficiently magnetize the magnetic markers, preferably the magnetic field generated by the permanent magnet or the exciting coil 15 should be uniform in the vertical direction.

Figure 10:
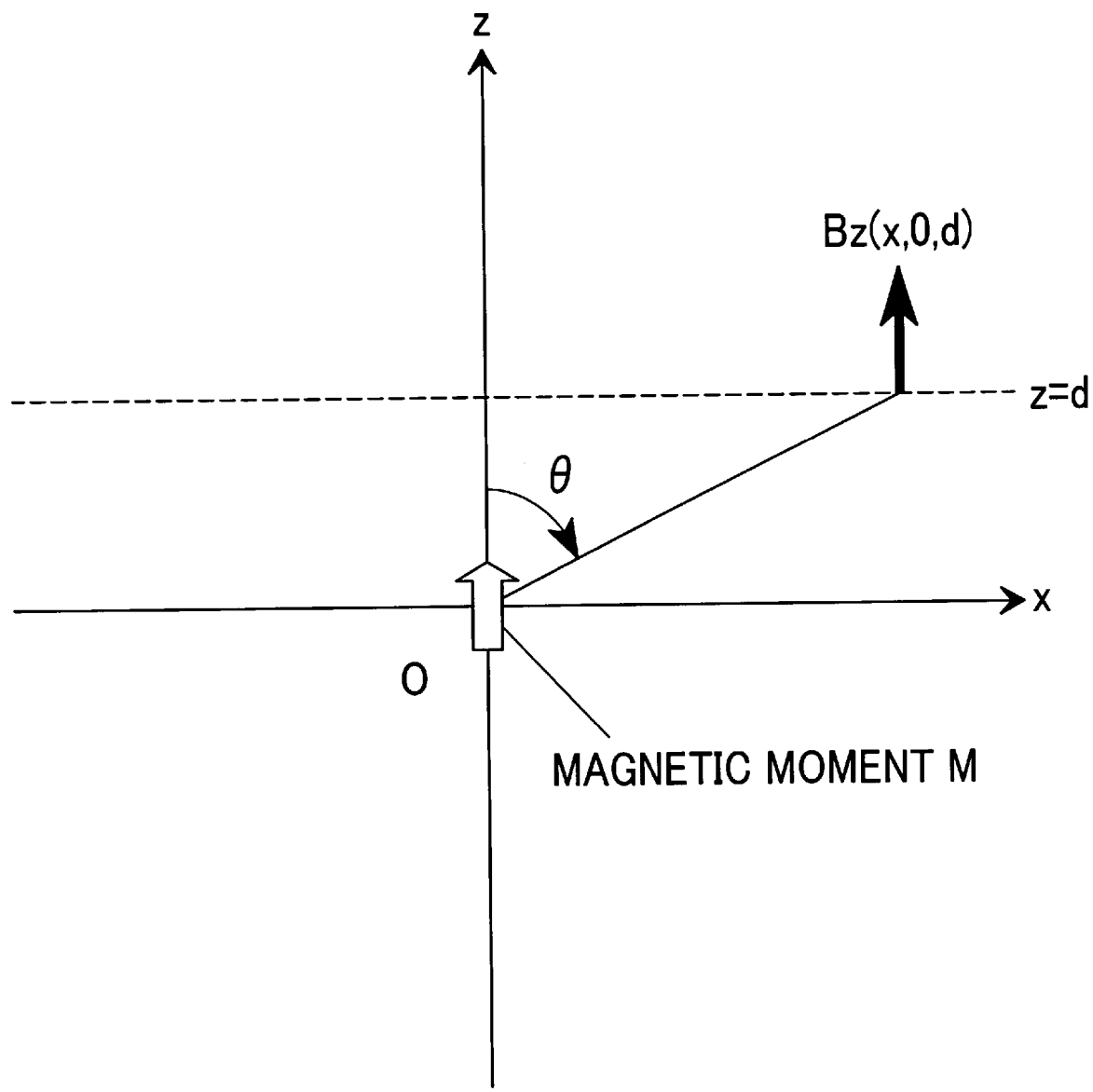
FIG. 10 is a graph for reviewing the mutual interference between magnetic signals of magnetic markers within the closest sample containers in the immunoassay system according to the invention, wherein the positional relationship of the distance between the pickup coil face of a magnetic sensor and the internal bottom of the sample container to a magnetic moment is illustrated.

FIG. 10 is a graph for reviewing the mutual interference between magnetic signals of magnetic markers within the closest sample containers 2 in the immunoassay system embodying the invention in this mode, wherein the positional relationship of the distance d between the pickup coil face of a magnetic sensor and the internal bottom of the sample container to a magnetic moment M is illustrated. FIG. 10 is used as a model diagram for figuring out the optimal conditions or arranging the sample containers 2 on the sample holder 3.

As shown in FIG. 10, the total sum of magnetic moments of magnetic markers combined with a living sample is supposed to exist at the origin O (0, 0, 0) as a magnetic moment M in the z direction=(0, 0, m). The magnetic field in the z direction at a point (x, 0, d) being supposed as $Bz(x)=Bz(x, 0, d)$, $\theta=\tan^{-1}(|x|/d)$ and $Bz(0)=m$, $Bz(x)/Bz(0)$ is represented by (Equation 1).

$$Bz(x)/Bz(0)=(1-3\sin^2\theta/2)\cos 3\theta \quad \text{(Equation 1)}$$

Figure 11:
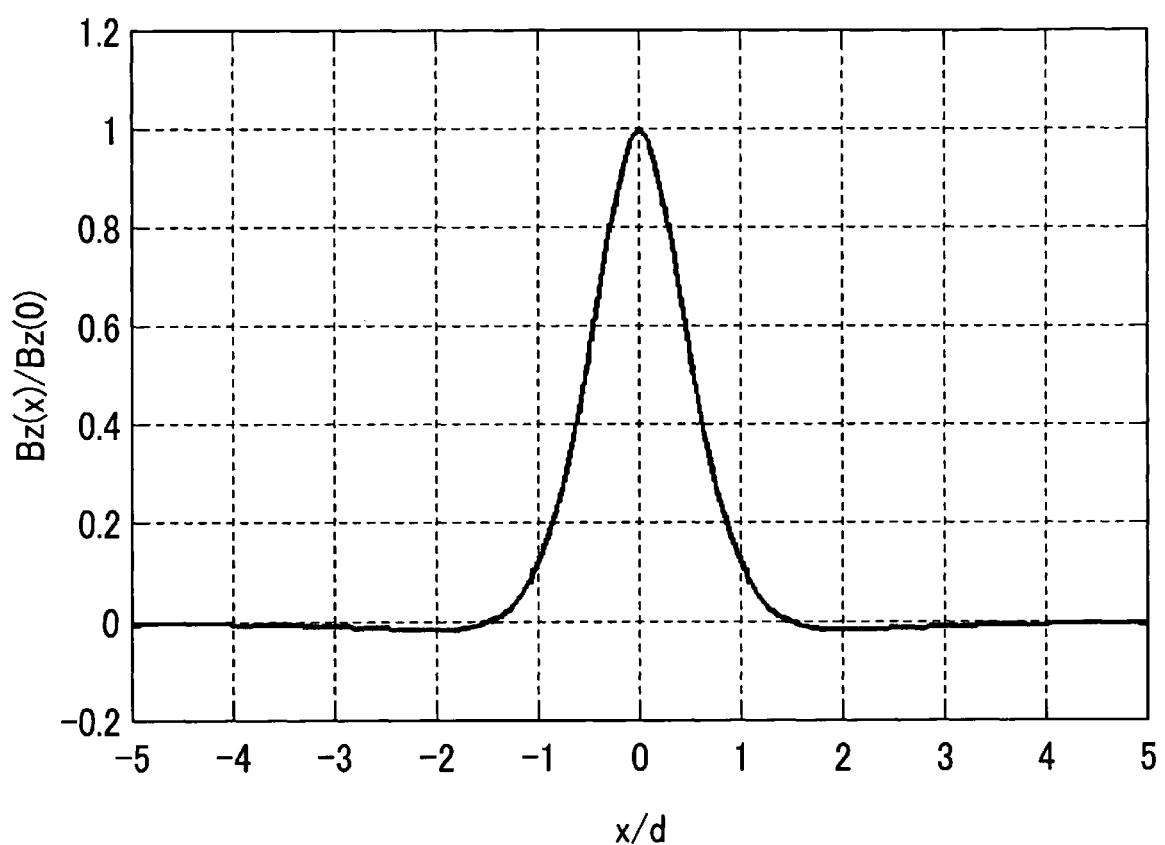
FIG. 11 is a characteristic line graph of the immunoassay system according to the invention, with (Equation 1) being given as a function of x/d.

FIG. 11 is a graph pertaining to the immunoassay system embodying the invention in this mode, expressing (Equation 1) as a function of x/d.

A signal deriving from a magnetic moment M attenuates as it moves away from the origin O (0, 0, 0), $Bz(x)/Bz(0)$ becoming 0 at $x=\square\sqrt{2}\approx\square\cdot$4d and becoming approximately 0 at $|x|/d \geq d\sqrt{2}\approx 1.4d$ as shown in FIG. 11. Therefore, in order to prevent the magnetic signals of magnetic markers in adjoining sample containers 2 from interfering with each other, preferably the distance between the sample containers 2 should beat least $d\sqrt{2}\approx 1.4d$. Thus, the distance between the pickup coil face of the magnetic sensor and the internal bottom of the sample container being represented by d, preferably the mutually closest sample containers should be arranged with a gap distance $\Delta$ of $d\sqrt{2}\approx 1.4d$ or more. To restrain interference between magnetic signals issued from adjoining sample containers, only the condition of $\Delta \geq d\sqrt{2}$ needs to be satisfied.

Figure 12:
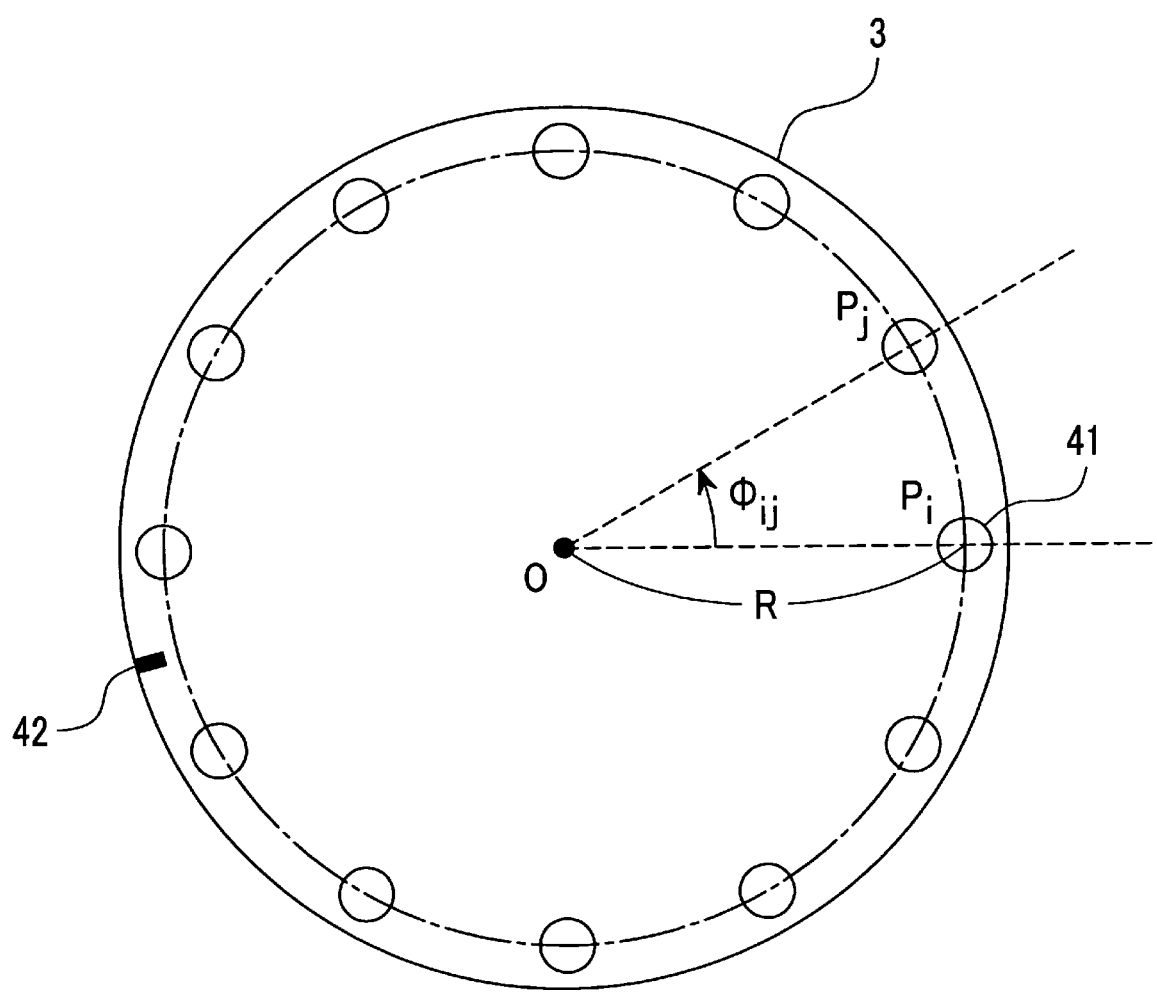
FIG. 12 shows a plan of one example of configuration of a disk-shaped sample holder in the immunoassay system according to the invention.

FIG. 12 shows a plan of one example of configuration of a disk-shaped sample holder in the immunoassay system embodying the invention in this mode.

The sample holder 3 is configured of a nonmagnetic material, such as a resin material or the like, and holes 41 for fixing the sample containers are arranged at equal intervals on a circle. The sample containers 2 are fixed and held in the holes 41. To enable the rotational position to be detected, the optically detectable marker 42 for position detection is formed in one position on the peripheral part of the sample holder 3 (either the upper or the lower face). The marker 42 for position detection should have a structure different in reflection factor from the sample holder 3. The position detection sensor 14 detects the marker 42 for position detection once every rotation.

As described with reference to FIG. 11, it is preferable for the sample containers 2 to be arranged with a gap distance $\Delta$ of $d\sqrt{2}$ or more on the same circle, the distance between the pickup coil face of the magnetic sensor and the internal bottom of the sample container 2 being represented by d. The center of rotation of the sample holder 3 is represented by O and the center of each sample container 2 by $P_j$ (j=1, ..., N; in the example shown in FIG. 11, N=12), $|OP_j|$=R and $\angle P_i OP_j = \phi_{ij}$ being supposed. R represents the radius of the circle on which the plurality of containers are to be arranged. A preferable arrangement of the sample containers 2 here is one satisfying the condition of $|P_i P_j|$=2R $\sin(\phi_{ij}/2) \geq d\sqrt{2} \approx 1.4d$, i.e. (Equation 2).

$$\phi_{ij} \geq 2 \sin^{-1}(d/(R(2))) \quad \text{(Equation 2)}$$

Figure 13:
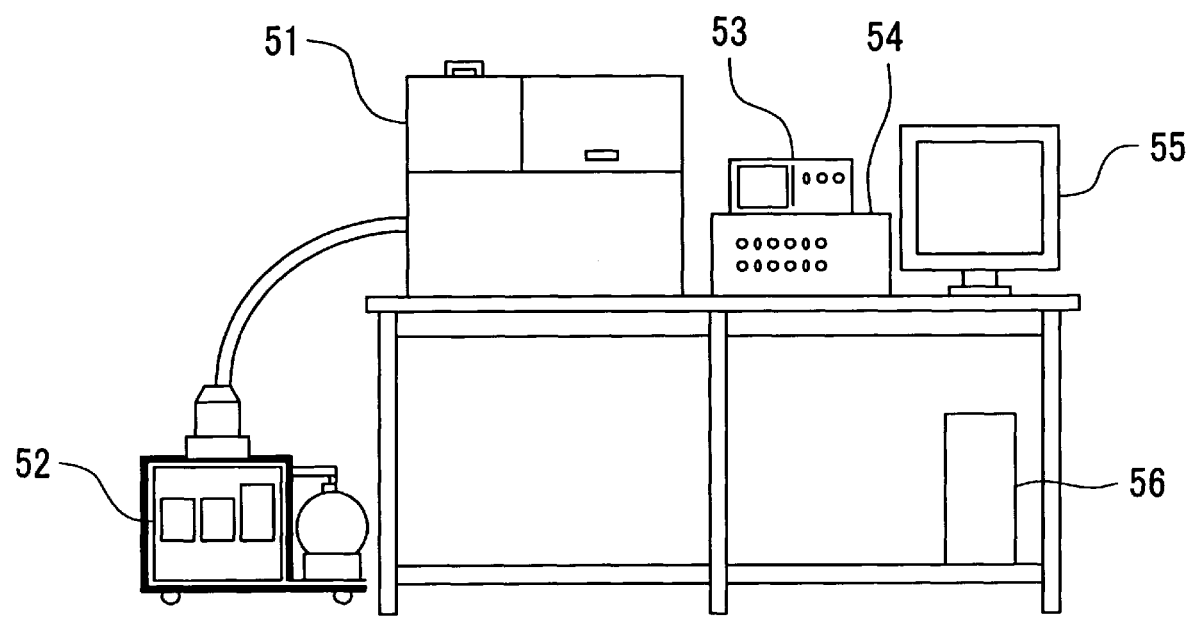
FIG. 13 shows the overall configuration of the immunoassay system according to the invention.

FIG. 13 shows the overall configuration of the immunoassay system embodying the invention in this mode.

By accommodating the principal part of the immunoassay system described with reference to FIG. 4 through FIG. 9 and FIG. 12 in a case 51 composed of an electroconductive material such as aluminum, the principal part of the immunoassay system can be protected and electromagnetically shielded.

An evacuating pump 52 evacuates the vacuum tank of the vacuum insulating container 6 in the case 51. The output of the SQUID 11 is processed by a control circuit 54 and a computer 56, and the results of measurement are displayed on an oscilloscope 53 and a display unit 55.

Figure 14:
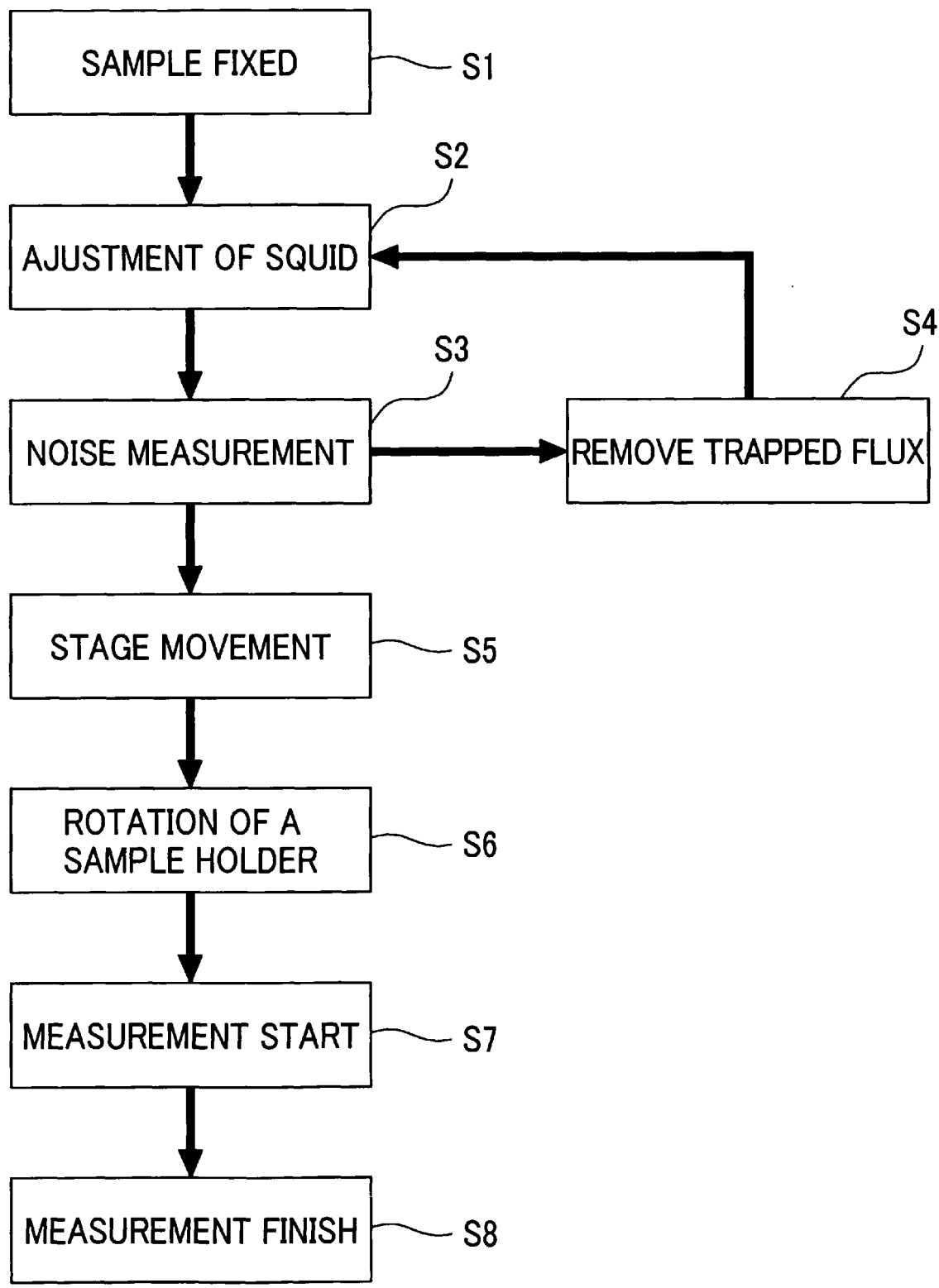
FIG. 14 is a flowchart of the procedure of measurement by the immunoassay system according to the invention.

FIG. 14 is a flowchart of the procedure of measurement by the immunoassay system embodying the invention in this mode.

First, the samples are prepared. Hereupon, as described with reference to FIG. 1, after combining a fixed antibody with each sample container 2, living samples are put into the sample containers 2; then, magnetic markers are added and mixed to cause antigen-antibody reaction to progress in the sample containers 2. Sample containers 2 in which this reaction has been completed are fixed to the sample holder 3 (step S1).

Next, the SQUID 11 is adjusted (step S2 through step S4). At step S2, the SQUID control circuit is adjusted to actuate an FLL circuit. In this state, the self-generated noise of the SQUID 11 is measured (step S3) and, if magnetic noise due to magnetic flux trapping is loud, the magnetic flux trapped by the SQUID 11 will be removed by heating the SQUID 11 with the light source for heating SQUID to or above the transition temperature and thereby returning it to a superconducting state (step S4).

When the adjustment of the SQUID 11 is completed by step S2 through step S4, the sample holder 3 is inserted by the moving stage 5 into the magnetic shields 1 and stops in the measuring position (step S5). Then, the sample holder 3 rotates at a prescribed rotation speed (step S6), and measurement is started (step S7). In this while, magnetization of magnetic markers is taking place at the same time outside the magnetic shields 1. The output of the SQUID 11 is inputted into the computer and undergoes processing of addition and averaging. Upon completion of the measurement, the sample holder 3 stops rotating and moves to its initial position to complete the sequence of processing (step S8).

An example of procedure of operating the immunoassay system of this embodiment will be described with reference to display screens on the display unit 55 shown in FIG. 15, FIG. 16 and, FIG. 17.

Figure 15:
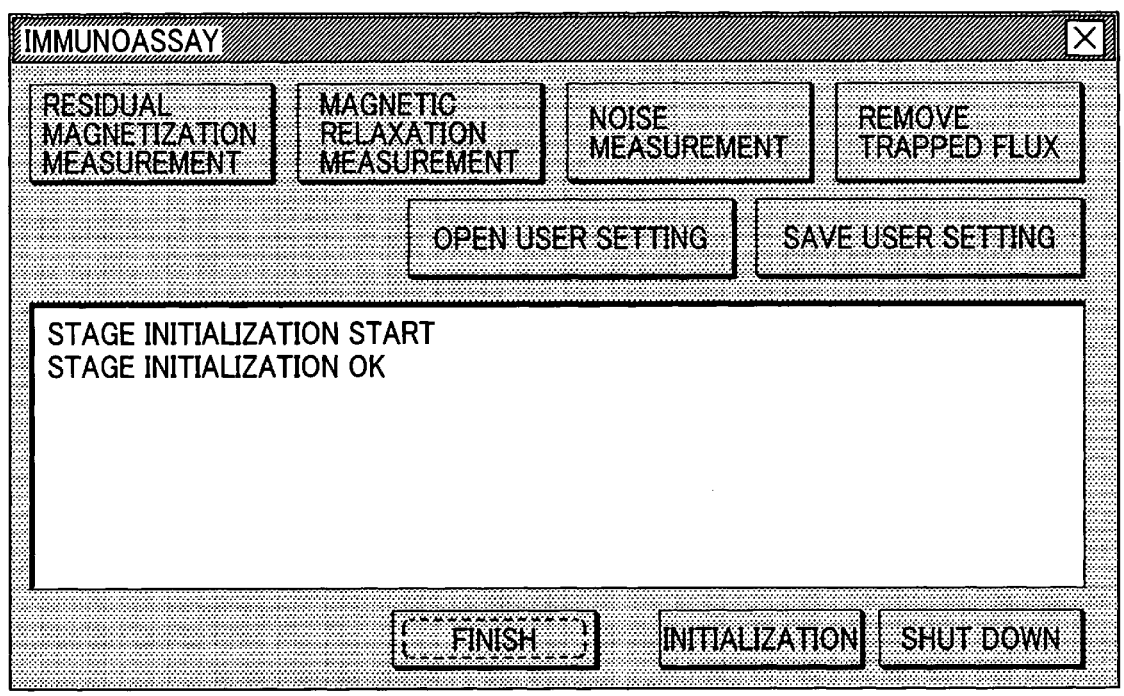
FIG. 15 shows an example of display screen in the initial state of the immunoassay system according to the invention.

FIG. 15 shows an example of display screen in the initial state of the immunoassay system embodying the invention in this mode.

FIG. 16 shows an example of display screen of setting measurement parameters in the immunoassay system embodying the invention in this mode.

Figure 17:
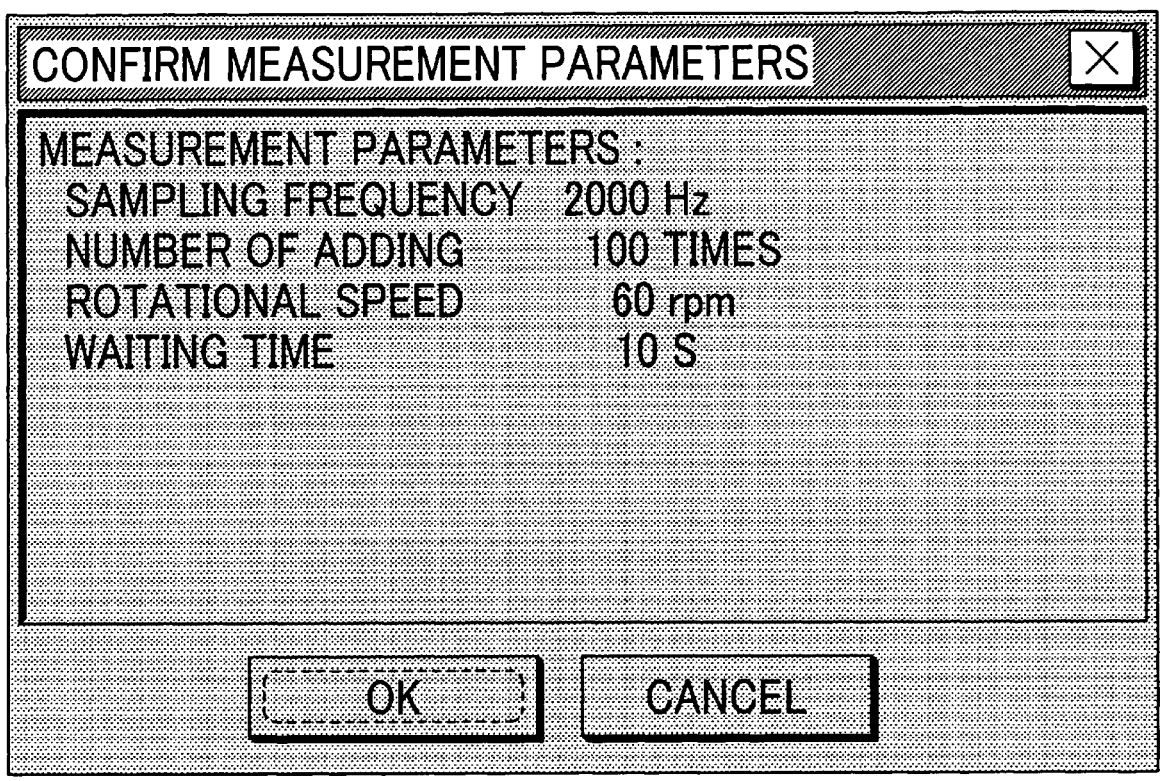
FIG. 17 shows an example of display screen of confirming the setting of measurement parameters in the immunoassay system according to the invention.

FIG. 17 shows an example of display screen of confirming the setting of measurement parameters in the immunoassay system embodying the invention in this mode.

In the initial screen illustrated in FIG. 15, "residual magnetization measurement", "magnetic relaxation measurement", "noise measure" and "remove trapped flux" modes are shown as alternative measurement modes, out of which the user can select one. If for instance the "noise measure" mode is selected, magnetic signals in the background are measured, and their frequency characteristics will be shown on the display screen. If the "residual magnetization measurement" or "magnetic relaxation measurement" mode is selected, the system will shift to the selected measurement mode, and the screen shown in FIG. 16 will be displayed. Hereupon, the respective measurement parameters for "sampling frequency", "number of additions", "rotation speed (number of revolutions)" and "waiting time" are set.

After the setting of measurement parameters, if "measurement start" is selected on the display screen shown in FIG. 16, the screen shown in FIG. 17 will be displayed. Here, "confirm measurement parameters" set on the screen shown in FIG. 16 is performed. For this measurement, the sampling frequency=200 Hz, the number of additions=100, the number of revolutions=60 rpm and the waiting time=10 s are set. If "OK" is selected here, the moving mechanism will start driving after the lapse of the waiting time=10 seconds, the sample holder 3 be inserted into the magnetic shields 1, and the rotation of the sample holder 3 started and, when the rotation speed (number of revolutions) of the sample holder 3 has reached 60 rpm, measurement of magnetic fields will be started.

As the number of additions is set to be 100 here, the measurement will end when the sample holder 3 has made 100 rotations. Since the rotation speed is 60 rpm, the sample holder 3 takes one second to make one rotation, and accordingly the length of time taken to add 100, signals to be measured is 100 seconds. Upon completion of the measurement, the rotation of the ample holder 3 is stopped, and the sample holder 3, driven by the moving mechanism, moves to its initial position outside the magnetic shields 1.

FIG. 18 are characteristic line graphs showing waveforms over time of magnetic signal detected by the immunoassay system in respect of samples in the 12 sample containers in the immunoassay system embodying the invention in this mode.

For the measurement graphed in FIG. 18, magnetic particles for instance nanomag-D in commercial name, a produce of Micromod) themselves were used as samples. The quantities of the samples used were, in terms of the weights of $Fe_3O_4$ alone, $2.3\times10^4$ pg for sample numbers 1, 2 and 3, $1.2\times10^3$ pg for sample numbers 4, 5 and 6, $2.3\times10^3$ pg for sample numbers 7, 8 and 9, and $1.2\times10^4$ pg for sample numbers 10, 11 and 12. The sample of j (j=1, . . . , 12) in sample number is held on the internal bottom of the sample container j (j=1, . . . , 12).

The radius of the rotational center of the sample holder 3 in the immunoassay system used for the measurement of FIG. 18 is R=75 mm, and the distance between the pickup coil face of the magnetic sensor and the internal bottom of the sample container 2 is d=1.5 mm (therefore $d\sqrt{2}$=2.1 mm). The 12 sample containers are arranged at equal intervals on a circle of radius R=75 mm. Therefore, the center-to-center distance of adjoining sample containers is 38.8 mm. The radius of the bottom of each sample container used is 2.5 mm, and the gap distance Δ between adjoining sample containers is (38.8−2× 2.5) mm=33.8 mm. Evidently the condition of $\Delta \geq d\sqrt{2}$ for restraining the interference between magnetic signals issued from magnetic particles in adjoining sample containers is satisfied.

The vertical axis in FIG. 18 represents the output result of the SQUID magnetic sensor (signal magnetic flux φs) and the horizontal axis, the length of time (in seconds). As shown in FIG. 18, large magnetic signals are obtained when the sample containers 2, rotated by the sample holder 3, pass underneath the SQUID magnetic sensor 11. Magnetic signals appear at (0 through 0.25) second and (0.75 through 1.00) second in the time position on the horizontal axis. They are attributable to, in the sequence in the direction of the time axis, samples in the sample containers 1, 2 and 3 and the sample containers 10, 11 and 12. In the case shown in FIG. 18, the rotation speed of the sample holder 3 is 60 rpm and the length of time taken to make one rotation is one second. Supposing that significant magnetic signals are detected from the samples in all the 12 sample containers 2, a significant signal is detected at intervals of 0.083 (=1/12) second. The positions of markers for position detection are detected with a position detection sensor, and the detected magnetic signals are added and averaged with these detected signals as sync signals.

Figure 18A:
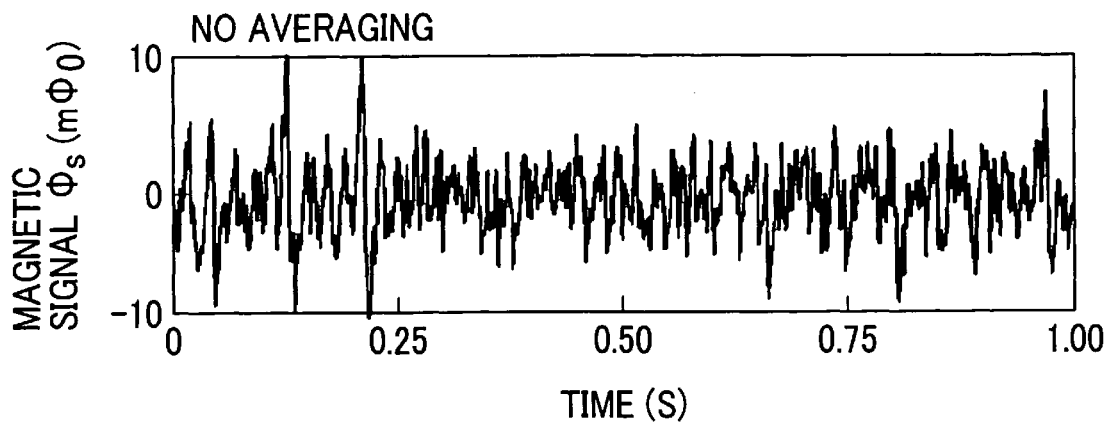
FIG. 18 are characteristic line graphs showing waveforms over time of magnetic signal detected by the immunoassay system according to the invention.
Figure 18B:
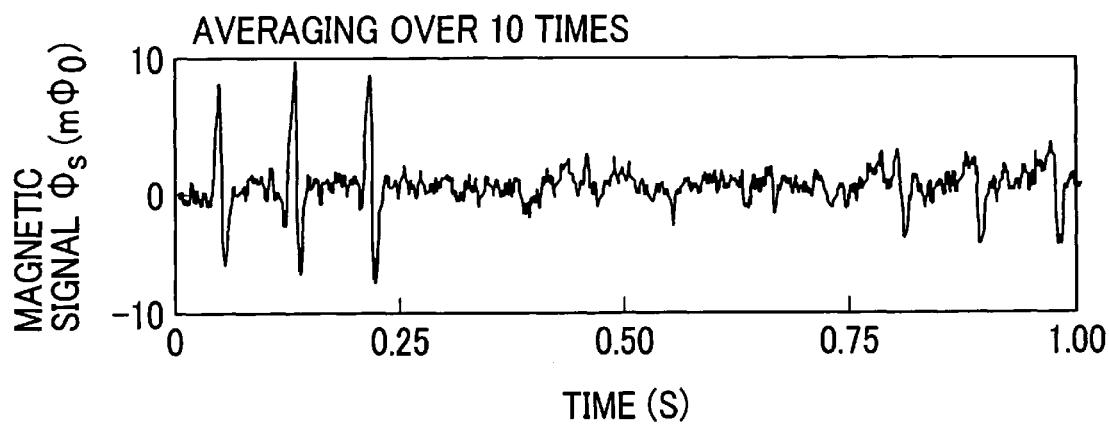
Figure 18C:
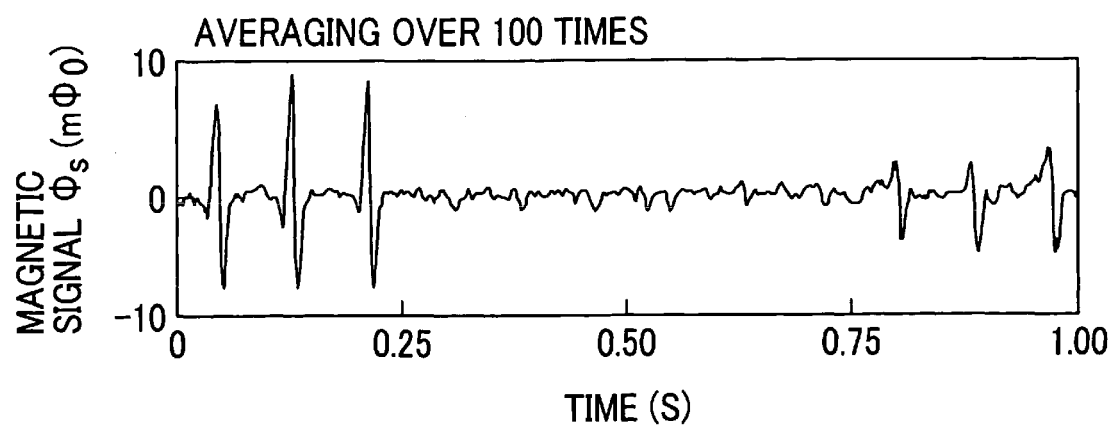

FIG. 18A shows magnetic signals having undergone no addition and averaging; FIG. 18B magnetic signals having undergone addition and averaging 10 times; and FIG. 18C, having undergone addition and averaging 100 times. As is evident from the comparison of signal wave forms shown in FIG. 18A, FIG. 18B and FIG. 18C, a significant improvement in the S/N ratio of the detected magnetic signals resulting from their addition and averaging can be performed. The improvement in the S/N ratio also makes possible more accurate measurement of the magnetic signals.

Figure 3:
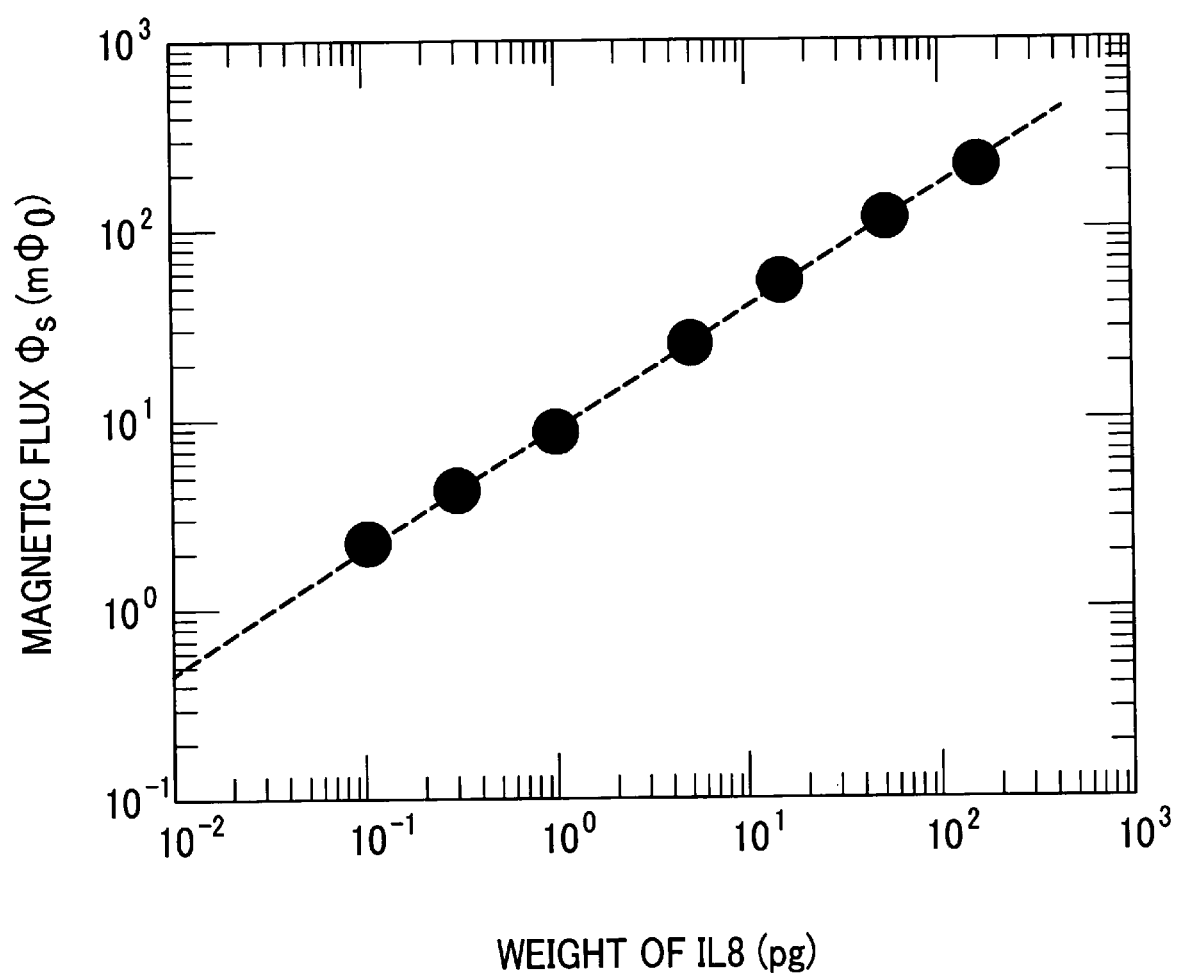
FIG. 3 shows an example of result of immunoassay using remanent magnetism according to the prior art.

Furthermore, addition and averaging even 100 times, for instance, takes only 100 seconds, and accordingly the configuration in which the sample holder 3 rotates makes possible acquisition of added and averaged data in a short period of time. The conventional method by which samples are moved linearly cannot achieve addition and averaging in such a short period. By converting the output of magnetic signals thereby obtained from the sample containers 2 into weights or mol counts by using a predetermined correlation as shown in FIG. 3, the quantity of antigen contained in each of the sample containers 2 can be detected.

Figure 19:
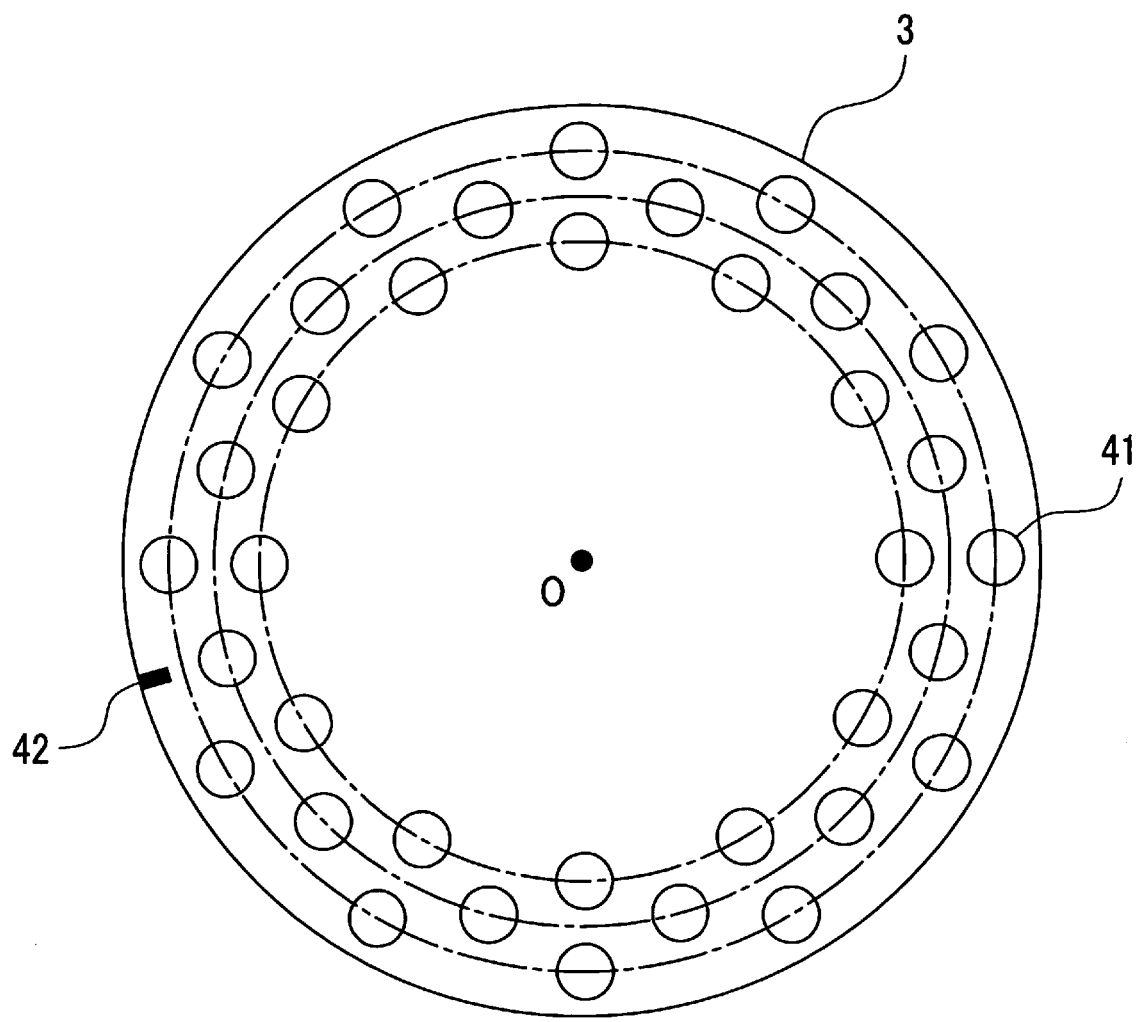
FIG. 19 shows a plan of another example of configuration of the disk-shaped sample holder in the immunoassay system according to the invention.

FIG. 19 shows a plan of another example of configuration of the disk-shaped sample holder, a disk-shaped the sample holder 3 in which sample containers 2 can be fixed on a plurality of circles differing in radius. FIG. 19 uses common reference numerals with FIG. 12.

The sample holder 3 is configured of a nonmagnetic material, such as a resin material or the like, as described with reference to FIG. 12, and holes 41 for fixing the sample containers are arranged on a plurality of circles differing in radius. In this example, 12 holes 41 for fixing the sample containers are arranged on each of the three concentric circles, or 36 holes in total. The sample containers 2 are fixed and held in the holes 41. To enable the rotational position to be detected, the optically detectable marker 42 for position detection is formed in one position on the peripheral part of the sample holder 3 (either the upper or the lower face). In order to fix a large number of samples to the disk-shaped sample holder, the holes 41 for fixing the sample containers are arranged in the sample holder 3 on the plurality of circles differing in radius as shown in FIG. 19. By increasing the number of sample containers 2 fixed to the sample holder 3, the throughput can be increased.

As described with reference to FIG. 11 and FIG. 12, it is preferable for the sample containers 2 to be arranged with a gap distance Δ of $d\sqrt{2}$ or more, the distance between the pickup coil face of the magnetic sensor and the internal bottom of the sample container 2 being represented by d.

Figure 20:
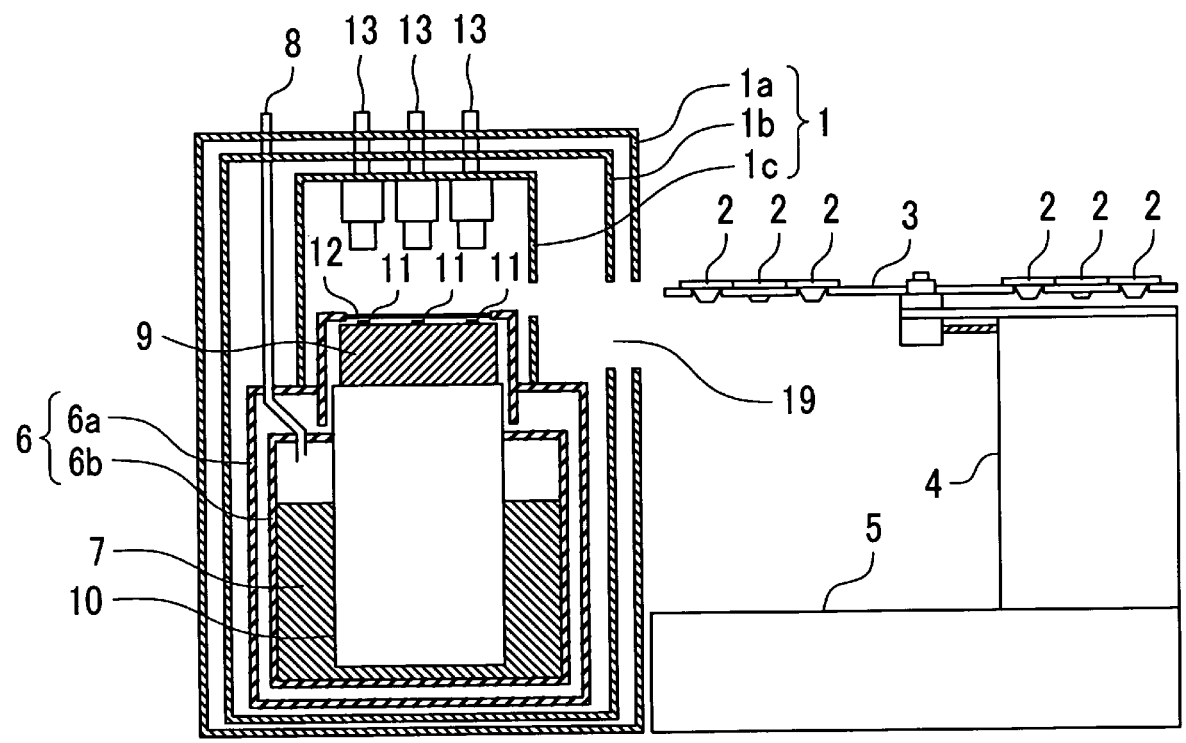
FIG. 20 contains a partial section of the immunoassay system using the disk-shaped sample holder of FIG. 19, illustrating the state of arrangement of constituent elements at the time of replacing the sample container and adjusting the control circuit of the SQUID.

FIG. 20 contains a partial section of the immunoassay system using the disk-shaped sample holder of FIG. 19, illustrating the state of arrangement of constituent elements at the time of replacing the sample container and adjusting the control circuit of the SQUID 11. FIG. 20 uses common reference numerals with FIG. 4.

The plurality of sample containers 2 are fixed the plurality of concentric circles differing in radius by the sample holder 3 described with reference to FIG. 19. Here is shown a case in which, as in FIG. 19, 12 holes 41 for fixing the sample containers are arranged on each of the three concentric circles, or 36 holes in total. This example, in order to detect the samples fixed on the three concentric circles more efficiently, has three SQUIDs 11 as shown in FIG. 20. The SQUIDs 11 are arranged at intervals so that each of the samples fixed on the three concentric circles pass right above one or another of the SQUIDs 11 when the sample holder 3 is inserted into the magnetic shields 1. Furthermore, since this configuration has three SQUIDs 11, it also has three light sources 13 for heating the SQUIDs. This configuration enables the number of samples detected per unit length of time to be increased.

Figure 21:
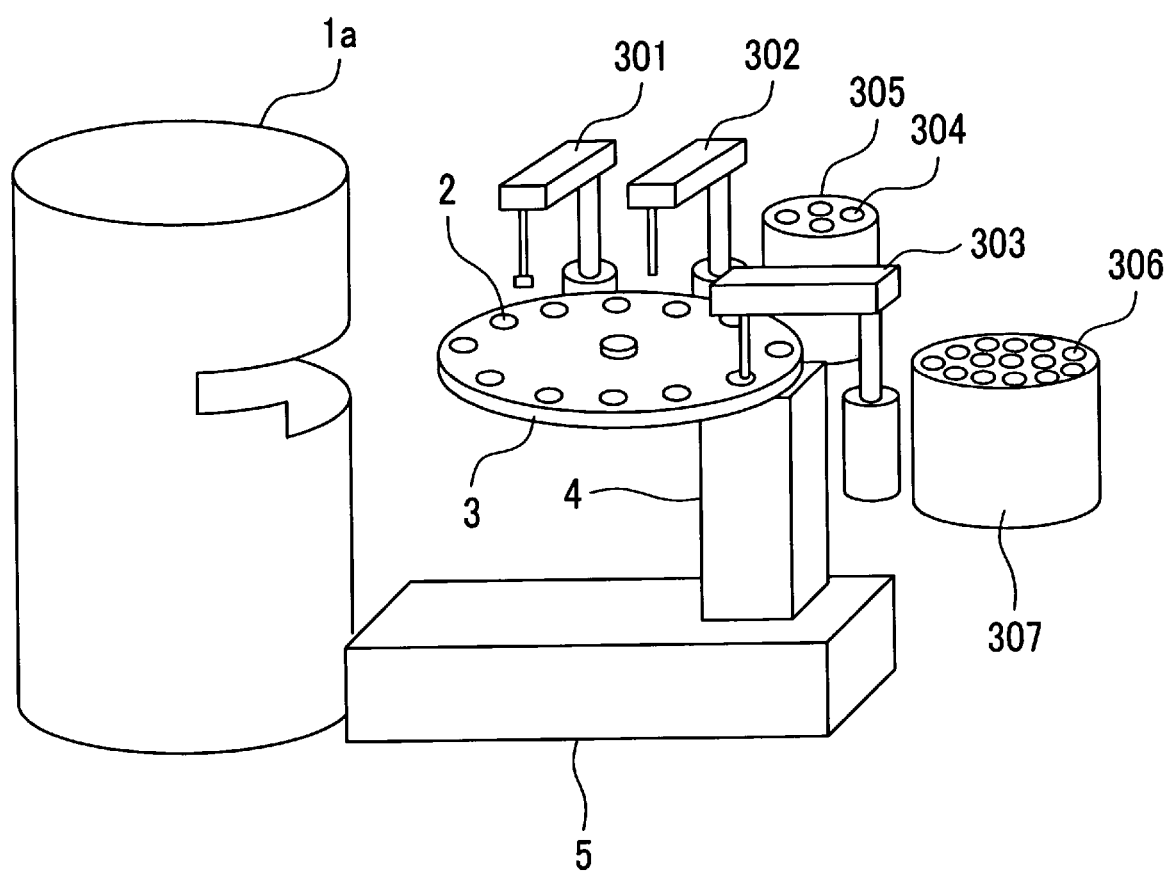
FIG. 21 shows a perspective view of a partial configuration of the immunoassay system according to the invention, illustrating the state of arrangement of constituent elements at the time of dispensing samples.

FIG. 21 shows a perspective view of a partial configuration of the immunoassay system embodying the invention in this mode, illustrating the state of arrangement of constituent elements at the time of dispensing samples.

The samples, which are the objects of assay, are dispensed into a plurality of sample containers 2 arranged on the sample holder 3 by a dispensing burette 303 from a plurality of sample containers 306 provided in a sample storage 307. The magnetic markers are similarly dispensed into the sample containers 2 by another dispensing burette 302 from a plurality of magnetic marker containers 304 provided in a magnetic marker storage 305. After that, the samples and the magnetic markers in the sample containers 2 are stirred by a stirring device 301. The dispensing burettes 302 and 303 and the stirring device 301 can be moved up and down and rotated by movable arms. After the mixed solution of samples and magnetic markers in the sample containers 2 is sufficiently stirred, antigen-antibody reaction is caused to progress by keeping the temperature of the mixed solution in the sample containers 2 at the optimal level for the antigen-antibody reaction, e.g. 37 ℃ to 40 ℃. After the lapse of a prescribed reaction period, the process will shift to step S2 described with reference to FIG. 14, followed by a similar process until step S8 to end the sequential procedure.

Characteristics of immunoassay systems according to the present invention will be summed up below.

(1) An immunoassay system according to the invention includes a disk-shaped sample holder which, composed of a nonmagnetic substance, fixes and holds on a circle a plurality of sample containers for accommodating marked samples, resulting from the marking of samples with magnetic particles by antigen-antibody reaction; rotating means for rotating the disk-shaped sample holder around its central shaft; magnetizing means for magnetizing the marked samples outside a magnetic shield; and a magnetic sensor for detecting within the magnetic shield magnetic fields generated from the marked samples which have been magnetized; wherein areas fixing and holding different ones of the sample containers are successively inserted into the magnetic shield through holes formed in the magnetic shield by the rotation of the disk-shaped sample holder; and the magnetization of the marked samples accommodated in first ones of the sample containers and the detection of magnetic fields generated from the marked samples accommodated in second ones of the sample containers, different from the first ones, are executed in parallel.

(2) In the system of (1) above, the magnetic sensor is provided with a pickup coil and a SQUID.

(3) In the system of (1) above, the outputs of the magnetic sensor are collected in a state in which the disk-shaped sample holder is rotating.

(4) The system of (1) above further has display means for displaying the signals detected by the magnetic sensor in a state in which the disk-shaped sample holder is rotating.

(5) The system of (1) above further has adding means for adding the signals detected by the magnetic sensor, in a state in which the disk-shaped sample holder is rotating, at every rotation of the disk-shaped sample holder which rotates a plurality of times and display means for displaying the result of addition by the adding means.

(6) In the system of (1) above, the rotating means is provided with an ultrasonic motor.

(7) In the system of (1) above, a marker for position detection for detecting the rotational position of the disk-shaped sample holder is disposed in the peripheral part of the disk-shaped sample holder.

(8) The system of (7) above is further provided with an optical sensor for detecting a laser beam irradiating the peripheral part of the disk-shaped sample holder and the laser beam reflected by the marker.

(9) In the system of (1) above, the magnetic sensor is provided with a SQUID formed of an oxide superconducting film, the system being further provided with a light source for irradiating the SQUID, and a trapped flux is removed by raising the temperature of the SQUID to or above the transition temperature by the irradiation with the light emitted from the light source.

(10) In the system of (1) above, the distance between the sample containers arranged adjoining each other is $d\sqrt{2}$ or more, where d is the distance between the face of the pickup coil and the internal bottom of the sample containers.

(11) In the system of (1) above, the plurality of sample containers are arranged on the same circle.

(12) An immunoassay system according to the invention includes a disk-shaped sample holder which, composed of a nonmagnetic substance, fixes and holds on the same circle a plurality of sample containers for accommodating marked samples, resulting from the marking of samples with magnetic particles by antigen-antibody reaction; rotating means for rotating the disk-shaped sample holder around its central shaft; magnetizing means for magnetizing the marked samples outside a magnetic shield; and a SQUID magnetic sensor for detecting within the magnetic shield magnetic fields generated from the marked samples which have been magnetized, wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed in parallel.

(13) An immunoassay system according to the invention includes a disk-shaped sample holder which, composed of a nonmagnetic substance, fixes and holds on the same circle a plurality of sample containers for accommodating marked samples, resulting from the marking of samples with magnetic particles by antigen-antibody reaction; rotating means for rotating the disk-shaped sample holder around its central shaft; magnetizing means for magnetizing the marked samples outside a magnetic shield; and a SQUID magnetic sensor for detecting within the magnetic shield magnetic fields generated from the marked samples which have been magnetized, wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed at the same time.

(14) An immunoassay system according to the invention includes a disk-shaped sample holder which, composed of a nonmagnetic substance, fixes and holds a plurality of sample containers for accommodating marked samples, resulting from the marking of samples with magnetic particles by antigen-antibody reaction; magnetizing means for magnetizing the marked samples; and a SQUID magnetic sensor for detecting magnetic fields generated from the marked samples which have been magnetized, wherein the distance between the sample containers arranged adjoining each other is $d\sqrt{2}$ or more, where d is the distance between the face of the pickup coil of the SQUID magnetic sensor and the internal bottom of the sample containers.

(15) An immunoassay system according to the invention includes a disk-shaped sample holder which, composed of a nonmagnetic substance, fixes and holds on a plurality of concentric circles differing in radius a plurality of sample containers for accommodating marked samples, resulting from the marking of samples with magnetic particles by antigen-antibody reaction; rotating means for rotating the disk-shaped sample holder around its central shaft; a plurality of magnetizing means for magnetizing the marked samples outside a magnetic shield; and a single or a plurality of SQUID magnetic sensors for detecting within the magnetic shield magnetic fields generated from the marked samples which have been magnetized, wherein areas fixing and holding different ones of the sample containers are successively inserted into the magnetic shield by the rotation of the disk-shaped sample holder; and the magnetization of the marked samples accommodated in a plurality of the sample containers and the detection of magnetic fields generated from the marked samples accommodated in a plurality of the sample containers, fixed and held in positions opposite the aforementioned sample containers, are executed in parallel.

(16) An immunoassay system according to the invention includes a dispensing burette sample for dispensing samples and antibodies for detection use marked with magnetic particles into sample containers; and a stirring mechanism for mixing solution in the sample containers, further having a disk-shaped sample holder which, composed of a nonmagnetic substance, fixes and holds on the same circle a plurality of sample containers for accommodating marked samples, resulting from the marking of samples with magnetic particles by antigen-antibody reaction; rotating means for rotating the disk-shaped sample holder around its central shaft; magnetizing means for magnetizing the marked samples outside a magnetic shield; and a SQUID magnetic sensor for detecting within the magnetic shield magnetic fields generated from the marked samples which have been magnetized, wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed in parallel.

Characteristics of immunoassay methods according to the present invention will be summed up below.

(1) An immunoassay method according to the invention includes a rotating step of rotating a disk-shaped sample holder which, composed of a nonmagnetic substance, fixes and holds on a circle a plurality of sample containers for accommodating marked samples, resulting from the marking of samples with magnetic particles by antigen-antibody reaction around its central shaft; a magnetizing step of magnetizing the marked samples outside a magnetic shield; and a detecting step of detecting within the magnetic shield with a magnetic sensor magnetic fields generated from the marked samples which have been magnetized; wherein areas fixing and holding different ones of the sample containers are successively inserted into the magnetic shield through holes formed in the magnetic shield by the rotation of the disk-shaped sample holder; and the magnetization of the marked samples accommodated in first ones of the sample containers and the detection of magnetic fields generated from the marked samples accommodated in second ones of the sample containers, different from the first ones of the sample containers, are executed in parallel.

(2) In the method of (1) above, the outputs of the magnetic sensor are collected in a state in which the disk-shaped sample holder is rotating.

(3) The method of (1) above further has a display step of displaying signals detected by the magnetic sensor in a state in which the disk-shaped sample holder is rotating.

(4) The method of (1) above further has an adding step of adding the signals detected by the magnetic sensor, in a state in which the disk-shaped sample holder is rotating, at every rotation of the disk-shaped sample holder which rotates a plurality of times and a display step of displaying the result of addition obtained at the adding step.

(5) The method of (1) above further has a step of detecting the rotational position of the disk-shaped sample holder by using a marker for position detection provided in the peripheral part of the disk-shaped sample holder.

(6) The method of (4) above further has a step at which the peripheral part of the disk-shaped sample holder is irradiated with a laser beam and a step at which the laser beam reflected by the marker is detected by an optical sensor.

(7) In the method of (1) above, the magnetic sensor is provided with a SQUID formed of an oxide superconducting film, the method further having a step of removing a trapped flux by raising the temperature of the SQUID to or above the transition temperature by irradiating the SQUID with light.

(8) An immunoassay method according to the invention includes a rotating step of rotating a disk-shaped sample holder for holding on the same circle a plurality of sample containers for accommodating marked samples, resulting from the marking of samples with magnetic particles by antigen-antibody reaction around its central shaft; a magnetizing step of magnetizing the marked samples outside a magnetic shield; and a detecting step of detecting within the magnetic shield with a SQUID magnetic sensor magnetic fields generated from the marked samples which have been magnetized; wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed in parallel.

(9) An immunoassay method according to the invention includes a rotating step of rotating a disk-shaped sample holder for holding on the same circle a plurality of sample containers for accommodating marked samples, resulting from the marking of samples with magnetic particles by antigen-antibody reaction around its central shaft; a magnetizing step of magnetizing the marked samples outside a magnetic shield; and a detecting step of detecting within the magnetic shield with a SQUID magnetic sensor magnetic fields generated from the marked samples which have been magnetized; wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed at the same time.

(10) An immunoassay method according to the invention includes a rotating step of rotating a disk-shaped sample holder for holding on a plurality of concentric circles differing in radius a plurality of sample containers for accommodating marked samples, resulting from the marking of samples with magnetic particles by antigen-antibody reaction around its central shaft; a magnetizing step of magnetizing the marked samples outside a magnetic shield; and a detecting step of detecting within the magnetic shield with a single or a plurality of SQUID magnetic sensors magnetic fields generated from the marked samples which have been magnetized; wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed at the same time.

(11) An immunoassay method according to the invention includes a dispensing step of dispensing samples and antibodies for detection use marked with magnetic particles into sample containers; a stirring step of mixing solution in the sample containers; a rotating step of rotating a disk-shaped sample holder which, composed of a nonmagnetic substance, fixes and holds on the same circle a plurality of sample containers for accommodating marked samples, resulting from the marking of samples with magnetic particles by antigen-antibody reaction around its central shaft; a magnetizing step of magnetizing the marked samples outside a magnetic shield; and a detecting step of detecting with a SQUID magnetic sensor within the magnetic shield magnetic fields generated from the marked samples which have been magnetized, wherein areas fixing and holding different ones of the sample containers are successively inserted into the magnetic shield by the rotation of the disk-shaped sample holder; and the magnetization of the marked samples accommodated in first ones of the sample containers and the detection of magnetic fields generated from the marked samples accommodated in second ones of the sample containers, fixed and held in positions opposite the first ones of the sample containers, are executed at the same time.

Characteristics of manners of arranging sample containers in the immunoassay system according to the present invention will be summed up below.

(1) By a manner of arranging sample containers in the immunoassay system according to the invention having a sample holder which fixes and holds a plurality of sample containers for accommodating marked samples, resulting from the marking of samples with magnetic particles by antigen-antibody reaction; magnetizing means for magnetizing the marked samples; and a SQUID magnetic sensor for detecting magnetic fields generated from the marked samples which have been magnetized, the plurality of sample containers are fixed and held by the sample holder and so arranged that the distance between the sample containers arranged adjoining each other be d√2 or more, where d is the distance between the face of the pickup coil of the SQUID magnetic sensor and the internal bottom of the sample containers.

(2) In the arranging manner of (1) above, a plurality of the sample containers are arranged on the same circle in the sample holder.

(3) In the arranging manner of (1) above, a plurality of the sample containers are arranged on a plurality of concentric circles differing in radius in the sample holder.

As hitherto described, the present invention can realize an immunoassay technique by which magnetic interference between adjoining sample containers is negligible and the antigen-antibody reaction of a large number of living samples can be efficiently detected with high sensitivity in a short period of time.

What is claimed is:

1. An immunoassay system comprising:
a disk-shaped sample holder which holds on a circle a plurality of sample containers for accommodating marked samples, resulting from marking of samples with magnetic particles by antigen-antibody reaction;
rotating means for rotating said disk-shaped sample holder around its central shaft;
magnetizing means for magnetizing said marked samples;
a magnetic sensor for detecting magnetic fields generated from said marked samples which have been magnetized; and
a magnetic shield surrounding said magnetic sensor,
wherein said plurality of sample containers are so configured as to be successively inserted from outside to inside of said magnetic shield by rotation of said disk-shaped sample holder;

said magnetizing means magnetize marked samples accommodated in at least one of the sample containers which is positioned outside said magnetic shield; said magnetic sensor detects marked samples accommodated in at least another one of the sample containers, which is different from said at least one of the sample containers and positioned within said magnetic shield, magnetic fields generated from said marked samples which have been magnetized; and the detection of said magnetic fields and said magnetization are executed in parallel.

2. The immunoassay system according to claim 1, wherein said magnetic sensor is provided with a pickup coil and a SQUID.

3. The immunoassay system according to in claim 1, wherein outputs of said magnetic sensor are collected in a state in which said disk-shaped sample holder is rotating.

4. The immunoassay system according to claim 1, further having display means for displaying signals detected by said magnetic sensor in a state in which said disk-shaped sample holder is rotating.

5. The immunoassay system according to claim 1, further having a processor for adding the signals detected by said magnetic sensor, in a state in which said disk-shaped sample holder is rotating and at every rotation of said disk-shaped sample holder; and a display for displaying a result of addition by said processor.

6. The immunoassay system according to claim 1, wherein said rotating means are provided with an ultrasonic motor.

7. The immunoassay system according to claim 1, wherein a marker for position detection for detecting a rotational position of said disk-shaped sample holder is disposed in a peripheral part of said disk-shaped sample holder.

8. The immunoassay system according to claim 7, further provided with an optical sensor for detecting a laser beam irradiating said peripheral part of said disk-shaped sample holder and said laser beam reflected by said marker.

9. The immunoassay system according to claim 1, wherein said magnetic sensor is provided with a SQUID formed of an oxide superconducting film, the system being further provided with a light source for irradiating said SQUID, and a trapped flux is removed by raising a temperature of said SQUID to or above a transition temperature by the irradiation with light emitted from said light source.

10. The immunoassay system according to claim 1, wherein a gap between said sample containers arranged adjoining each other is d√2 or more, where d is a distance between a face of said pickup coil and an internal bottom of said sample containers.

11. The immunoassay system according to claim 10, wherein said plurality of sample containers are arranged on said same circle or concentric circles.

12. An immunoassay system comprising:
a disk-shaped sample holder which holds on the same circle a plurality of sample containers for accommodating marked samples, resulting from marking of samples with magnetic particles by antigen-antibody reaction;
rotating means for rotating said disk-shaped sample holder around its central shaft; magnetizing means for magnetizing said marked samples;
a SQUID magnetic sensor for detecting magnetic fields generated from said marked samples which have been magnetized; and
a magnetic shield surrounding said SQUID magnetic sensor, wherein said plurality of sample containers are so configured as to be successively inserted from outside to inside of said magnetic shield by rotation of said disk-shaped sample holder;

said magnetizing means magnetize marked samples accommodated in at least one of the sample containers which is positioned outside said magnetic shield; said SQUID magnetic sensor detects marked samples accommodated in at least another one of the sample containers, which is different from said at least one of the sample containers and positioned within said magnetic shield, magnetic fields generated from said marked samples which have been magnetized; and the detection of said magnetic fields and said magnetization are executed in parallel.

13. The immunoassay system according to claim 12, wherein a gap between said sample containers arranged adjoining each other is $d\sqrt{2}$ or more, where d is a distance between a face of the pickup coil of said SQUID magnetic sensor and an internal bottom of said sample containers.

14. An immunoassay system comprising:

a disk-shaped sample holder which holds on the same circle a plurality of sample containers for accommodating marked samples, resulting from marking of samples with magnetic particles by antigen-antibody reaction;

rotating means for rotating said disk-shaped sample holder around its central shaft;

magnetizing means for magnetizing said marked samples;

a SQUID magnetic sensor for detecting magnetic fields generated from said marked samples which have been magnetized; and a magnetic shield surrounding said SQUID magnetic sensor, wherein said plurality of sample containers are so configured as to be successively inserted from outside to inside of said magnetic shield by rotation of said disk-shaped sample holder;

said magnetizing means magnetize marked samples accommodated in at least one of the sample containers which is positioned outside said magnetic shield; said SQUID magnetic sensor detects marked samples accommodated in at least another one of the sample containers, which is different from said at least one of the sample containers and positioned within said magnetic shield, magnetic fields generated from said marked samples which have been magnetized; and the detection of said magnetic fields and said magnetization are executed at the same time.

* * * * *